United States Patent [19]

Sayers et al.

[11] Patent Number: 5,604,300
[45] Date of Patent: Feb. 18, 1997

[54] CROSSLINK TEST METHOD

[75] Inventors: Norman A. Sayers; Russell D. Taylor, both of Duncan; David L. Lord, Marlow, all of Okla.; Audis C. Byrd, Katy, Tex.

[73] Assignee: Halliburton Company, Duncan, Okla.

[21] Appl. No.: 515,497

[22] Filed: Aug. 15, 1995

[51] Int. Cl.[6] .................................................. G01N 11/14
[52] U.S. Cl. .................... 73/54.31; 73/54.35; 73/54.028; 137/4
[58] Field of Search ............................ 73/54.31, 54.35, 73/54.32, 54.33, 54.29, 54.28; 137/4

[56] References Cited

U.S. PATENT DOCUMENTS

| | | | |
|---|---|---|---|
| 1,321,736 | 11/1919 | Green | 73/54.31 |
| 2,096,222 | 10/1937 | Bock | 265/11 |
| 2,122,765 | 7/1938 | Weiler | 265/11 |
| 2,237,743 | 4/1941 | McIntyre | 265/11 |
| 2,266,733 | 12/1941 | Bays et al. | 265/11 |
| 2,603,087 | 7/1952 | Von Hortenau | 73/59 |
| 2,683,984 | 7/1954 | Boyle et al. | 73/59 |
| 2,952,152 | 9/1960 | Fisher et al. | 73/17 |
| 3,053,079 | 9/1962 | Miller et al. | 73/60 |
| 3,269,171 | 8/1966 | Bruss et al. | 73/60 |
| 3,285,057 | 11/1966 | De Zurik | 73/59 |
| 3,286,510 | 11/1966 | Parker | 73/53 |
| 3,292,423 | 12/1966 | Banks | 73/60 |
| 3,347,089 | 10/1967 | Perry | 73/59 |
| 3,402,729 | 9/1968 | Richmond et al. | 137/92 |
| 3,435,666 | 4/1969 | Fann | 73/60 |
| 3,520,657 | 7/1970 | Steinberg et al. | 23/230 |
| 3,751,975 | 8/1973 | Katsura | 73/59 |
| 3,875,791 | 4/1975 | Fitzgerald et al. | 73/59 |
| 4,033,557 | 7/1977 | Kromer et al. | 259/192 |
| 4,065,959 | 1/1978 | Richardson | 73/56 |
| 4,151,744 | 5/1979 | Hemmings | 73/54 |
| 4,157,036 | 6/1979 | Kivenson | 73/290 |
| 4,175,425 | 11/1979 | Brookfield | 73/59 |

(List continued on next page.)

FOREIGN PATENT DOCUMENTS

| | | |
|---|---|---|
| 1184119 | 12/1964 | Germany. |
| 415553 | 3/1972 | U.S.S.R.. |
| 594438 | 9/1976 | U.S.S.R.. |
| 650009 | 4/1979 | U.S.S.R.. |
| 670855 | 6/1979 | U.S.S.R.. |

OTHER PUBLICATIONS

Society of Petroleum Engineers publication entitled "Attachment A– SPE #18209—New Insights on the Rheological Behavior of Delayed Crosslinked Fracturing Fluids" by J. R. Cameron, D. C. Gardner and R. W. Veatch, Jr., 1988.
Society of Petroleum Engineers publication entitled "SPE 9285 –Transition Time of Cement Slurries Between the Fluid and Set State" by Fred L. Sabins, John M. Tinsley and David L. Sutton, 1980.

(List continued on next page.)

*Primary Examiner*—Hezron E. Williams
*Assistant Examiner*—J. David Wiggins
*Attorney, Agent, or Firm*—Stephen R. Christian; E. Harrison Gilbert, III

[57] ABSTRACT

Automated objective crosslink time and crosslink temperature determinations are provided in a method of testing for chemical crosslinking of a fluid. A fluid having a crosslinking agent is placed in a vessel and a paddle is rotated through the fluid in the vessel at substantially a constant rotational speed. A paddle torque parameter is sensed at sequential times and digital signals are encoded to define digital torque data representing values of the sensed torque parameter. In response to stored digital torque data and digital time data, a baseline torque parameter value and a change in the digital torque data representing increasing torque of the paddle are determined. In response to the baseline torque parameter value and the change in the digital torque data, a crosslink time for the fluid is determined. A crosslink temperature can also be determined. This is determined in response to the crosslink time and stored digital temperature data that has been obtained at sequential times.

17 Claims, 7 Drawing Sheets

U.S. PATENT DOCUMENTS

| | | | |
|---|---|---|---|
| 4,184,364 | 1/1980 | Du Bae | 73/54 |
| 4,283,938 | 8/1981 | Epper et al. | 73/59 |
| 4,299,118 | 11/1981 | Gau et al. | 73/59 |
| 4,448,061 | 5/1984 | Brookfield | 73/59 |
| 4,466,276 | 8/1984 | Ruyak et al. | 73/59 |
| 4,484,468 | 11/1984 | Gau et al. | 73/60 |
| 4,485,450 | 11/1984 | Characklis et al. | 364/550 |
| 4,571,988 | 2/1986 | Murphy et al. | 73/60 |
| 4,612,800 | 9/1986 | Erian | 73/54 |
| 4,622,846 | 11/1986 | Moon, Jr. et al. | 73/59 |
| 4,648,264 | 3/1987 | Freese et al. | 73/64.1 |
| 4,668,911 | 5/1987 | Mueller et al. | 324/208 |
| 4,778,631 | 10/1988 | Cobbs, Jr. et al. | 261/128 |
| 4,823,594 | 4/1989 | Gray | 73/54 |
| 4,829,811 | 5/1989 | Ehlert et al. | 73/59 |
| 4,879,897 | 11/1989 | Booth et al. | 73/59 |
| 5,167,143 | 12/1992 | Brookfield | 73/54.23 |
| 5,321,974 | 6/1994 | Hemmings et al. | 73/54.31 |
| 5,353,827 | 10/1994 | Bouchard et al. | 137/1 |

OTHER PUBLICATIONS

Halliburton Services publication entitled "Cement Measuring and Testing Instruments," published more than one year prior to the filing date.

Halliburton Services publication entitled "Cement Slurry Measurement Instruments for Laboratory," published more than one year prior to the filing date.

Halliburton Services publication entitled "Ultra-sonic Cement Analyzer," published more than one year prior to the filing date.

Brookfield publication entitled "TT200 Process Viscometer," published more than one year prior to the filing date.

Brookfield publication entitled "TT100 In-Line Viscometer," published more than one year prior to the filing date.

American Petroleum Institute publication entitled "Section 8–Thickening Time Tests (Specification Test)," published more than one year prior to the filing date.

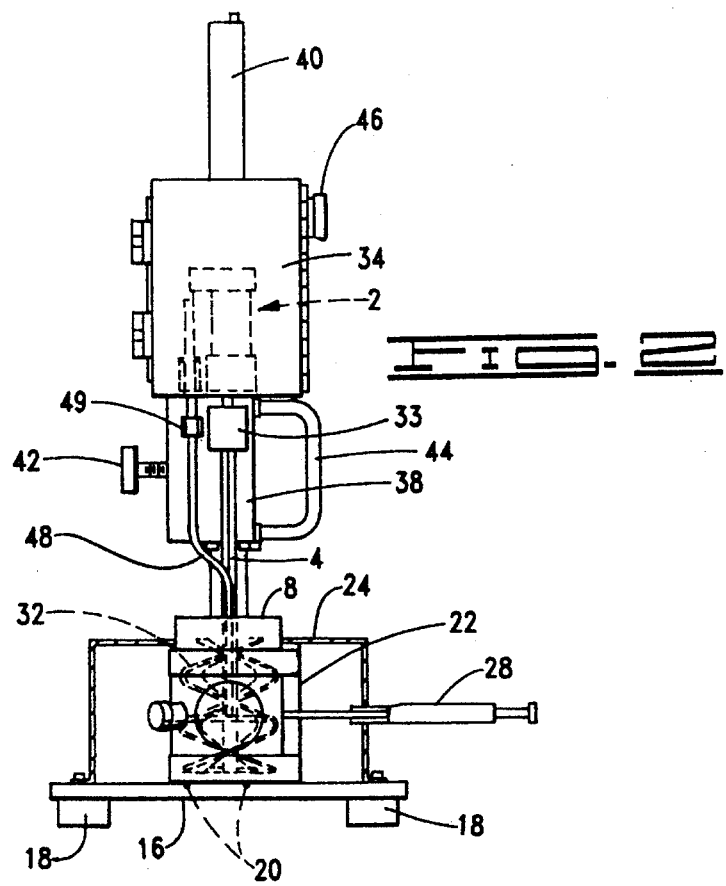
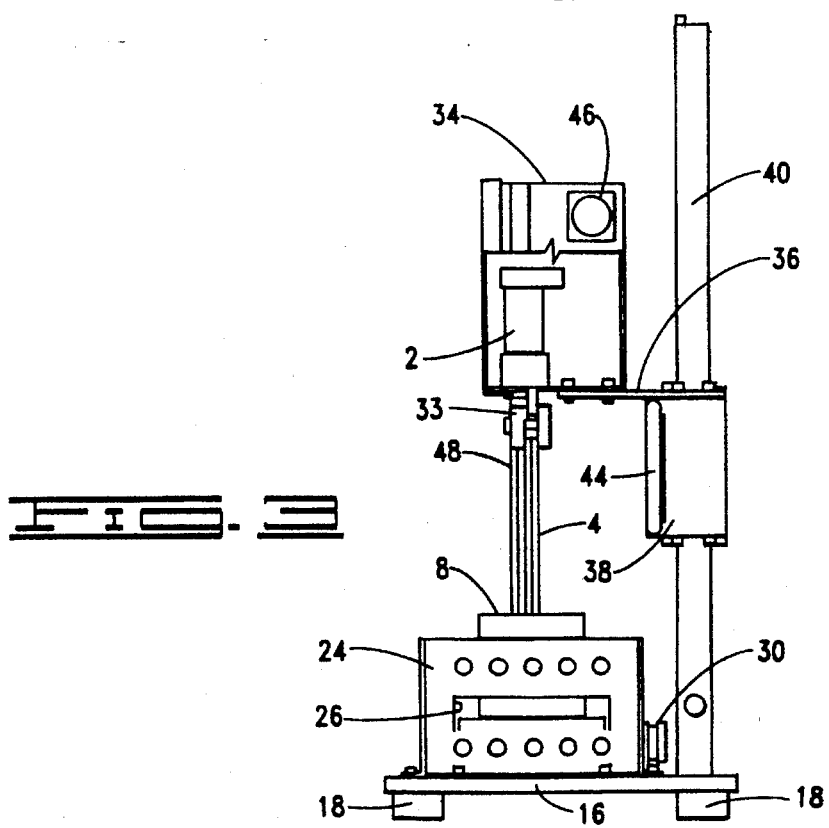

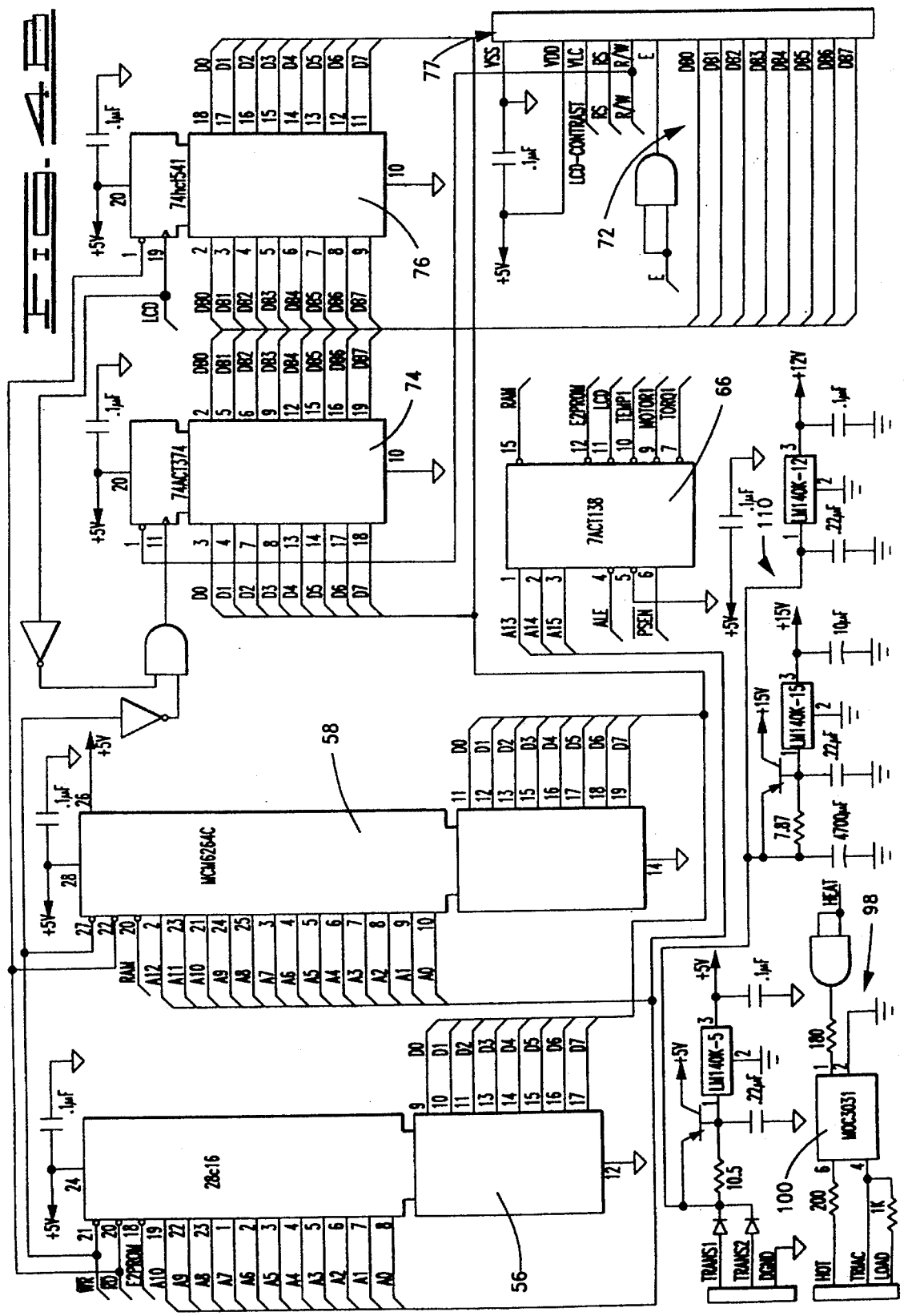

CROSSLINK TEST METHOD

BACKGROUND OF THE INVENTION

This invention relates to methods for testing fluids that have one or more crosslinking agents in them. More particularly, the invention provides a method by which crosslink time, and preferably crosslink temperature as well, can be determined in a manner contemplated to standardize the testing of crosslinked fluids.

In the process of stimulating oil and gas wells, various fluids are used, such as solutions of high molecular weight oil or water soluble polymers. Some of these include particulate material, such as sand. The viscosity of these fluids can be increased by a chemical process known as crosslinking. Crosslinking occurs by introducing into the fluid an ionic agent (the crosslinking agent, or crosslinker), such as transition metal or borate ions. The crosslinker bonds polymer molecules in the primary fluid together, thereby increasing the polymer molecular weight and therefore increasing the viscosity of the resulting mixture. The onset of this phenomenon is monitored and controlled during various types of stimulation treatments to help provide a fluid that will perform as desired after time lapse or temperature change or both.

One critical parameter that needs to be determined for a crosslinked fluid is crosslink time. The elapsed time from crosslinker addition and/or temperature change to the onset of crosslinking is defined as crosslink time. A knowledge of crosslink time is important for a number of reasons. For example, consistent crosslink time measurements throughout a treatment are an indication that operating conditions such as fluid pH, crosslinker addition rate, and crosslinker composition are being controlled in a satisfactory manner. In addition to verification of quality control, crosslink time can have a significant effect on both downhole and surface treating conditions. It is generally desirable to have the onset of crosslinking occur downhole just upstream of the perforations. Increased viscosity from crosslinking helps to transport particulates through the perforations and into the fracture. If the onset of crosslinking occurs shortly after the fluid enters the treating string, increased viscosity from crosslinking will increase surface treating pressure and hence increase the power requirements for Completion of the treatment. Although crosslink time can be shown to be important there has not been a standardized method of determining crosslink time such that crosslink time can be accurately and consistently defined and such that various crosslinked fluids can be compared with each other.

In the prevalent crosslink test method that has been used to determine crosslink time, an operator places a small sample of the fluid in a cup in a heated bath, stirs the sample, visually observes a thickening of the fluid, and performs a subjective "lip" test. This lip test includes removing the cup from the heated bath, tilting the cup until the fluid starts to flow over the lip of the cup, and then righting the cup. If the partially overflamed portion of fluid draws back into the cup when it is righted, the crosslinking is considered to have occurred and the time is noted.

Crosslink temperature is another important parameter that is typically determined with the crosslink time. In the "lip" test method the temperature of the heated water bath is set to provide uniform heating from the starting temperature of the fluid to the well perforation temperature over a time period equal to the fluid transport time down the treatment string. If crosslinking is observed before the perforation temperature is reached, the temperature of the sample at the crosslink time is recorded as the crosslink temperature. If the perforation temperature is reached before the sample crosslinks, the sample is removed from the heated bath and maintained at the perforation temperature for the duration of the test.

To obtain the aforementioned benefits of standardized crosslink testing, there is the need for an automated objective method of testing for crosslinking of a fluid whereby crosslink time and preferably crosslink temperature as well can be objectively determined.

SUMMARY OF THE INVENTION

The present invention overcomes the above-noted and other shortcomings of the prior art by providing a novel and improved method of testing for crosslinking of a fluid. More particularly, the invention provides for automated, consistent testing for objectively determining crosslink time and crosslink temperature of fluids having crosslinking agents.

The present invention better defines the crosslink phenomenon of a fluid and aids in the testing and comparison of various fluids, including stimulation fluid systems for oil and gas wells. For example, using the present invention, different crosslinkers can be compared to each other and different temperature effects on the same crosslinker can be compared. As to crosslink time determination itself, the present invention can be used without knowing what is in a particular sample (however, heater control requires knowledge of fluid and sand concentration in the sample). The present invention can be made portable for field or laboratory use. It is contemplated that the present invention can help standardize the laboratory and field testing of the crosslink phenomenon. Specifically, it is contemplated that the present invention can provide the long needed standardized definition of crosslink time and temperature.

The method of testing for crosslinking of a fluid comprises placing in a vessel a fluid having a crosslinking agent and rotating a paddle through the fluid in the vessel at substantially a constant rotational speed. The method further comprises sensing, at sequential times, a parameter related to paddle torque. Digital signals are encoded to define digital torque data representing values of the sensed torque parameter and to define digital time data representing corresponding sequential times. The method still further comprises determining, in response to digital torque data and digital time data, a baseline torque parameter value and a change in the digital torque data representing increasing torque of the paddle (and thus increasing crosslinking and resulting viscosity of the fluid). The method also comprises determining, in response to the baseline torque parameter value and the change in the digital torque data, a crosslink time for the fluid. In the preferred embodiment described below, the crosslink time is determined by computing the time point at which a line containing a maximum change in the digital torque data coincides with the baseline torque parameter value.

The method can also test for crosslink temperature. This further comprises: heating the fluid; sensing temperature of the fluid during the sequential times and encoding digital signals to define digital temperature data at corresponding sequential times; and determining, in response to the crosslink time and the digital temperature data, a crosslink temperature. In the preferred embodiment, the crosslink temperature is the temperature determined from the digital temperature data at the sequential time or times corresponding to the crosslink time.

Therefore, from the foregoing, it is a general object of the present invention to provide a novel and improved method of testing for crosslinking of a fluid. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 2 is an elevational view of a particular implementation of the motor/speed sensor/vessel/heater apparatus of the system of FIG. 1.

FIG. 3 is another elevational view of the apparatus shown in FIG. 2.

FIG. 6 is a chart graphically illustrating the method by which crosslink time and temperature are determined in the preferred embodiment of the present invention.

DETAILED DESCRIPTION OF PREFERRED EMBODIMENT

Figure 1:
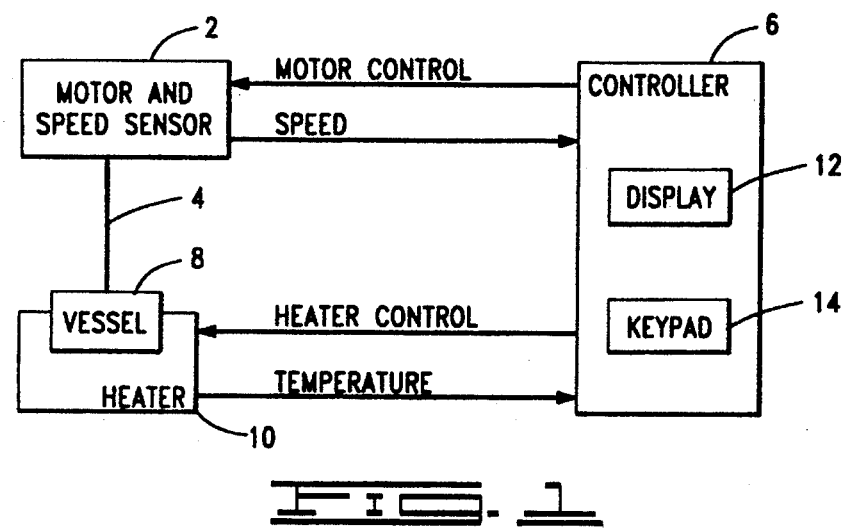
FIG. 1 is a block diagram of a system for implementing the method of the present invention.
Figure 4:
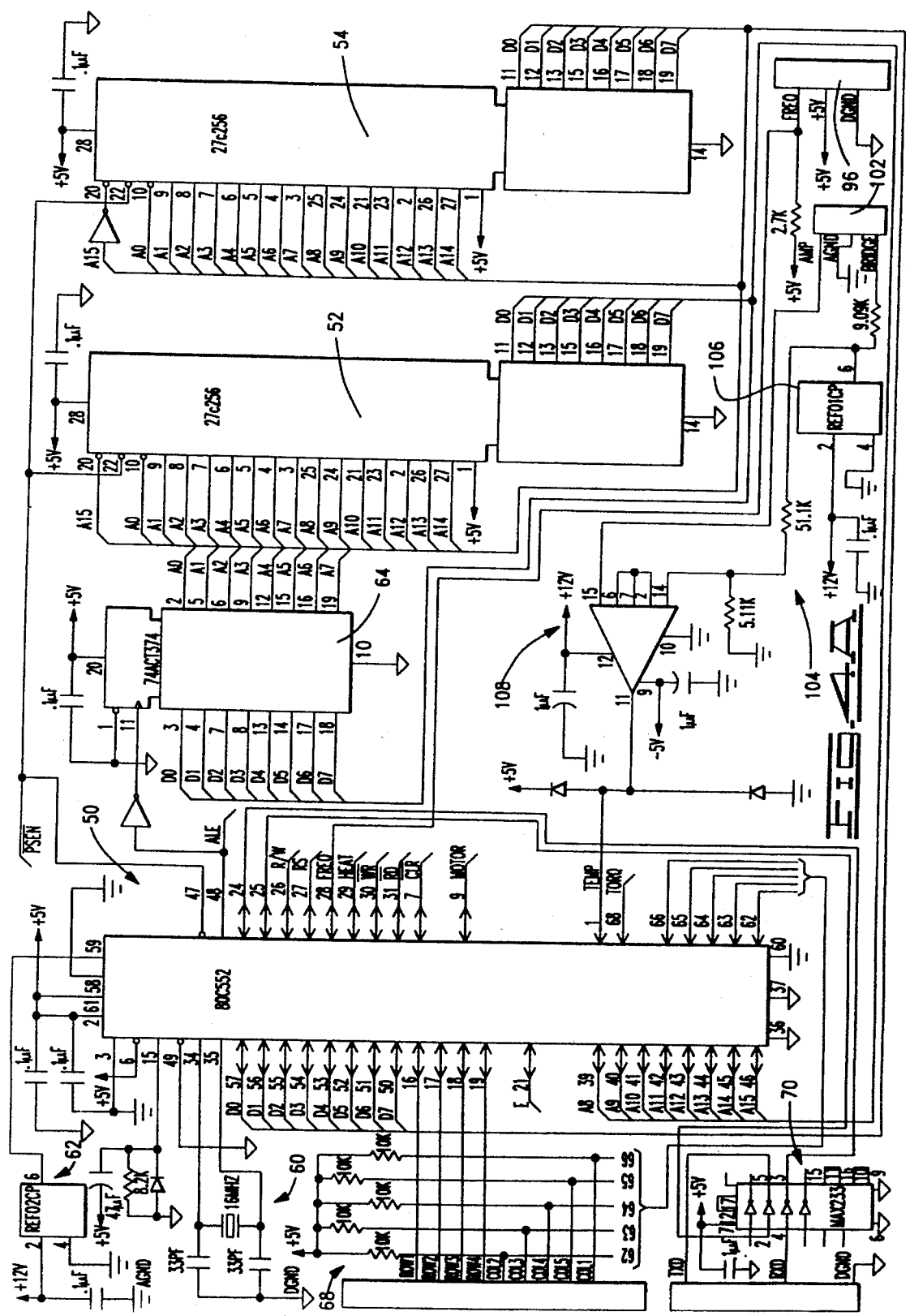
FIGS. 4A–4C are a schematic circuit diagram of a particular implementation of the controller apparatus of the system of FIG. 1.
Figure 4:
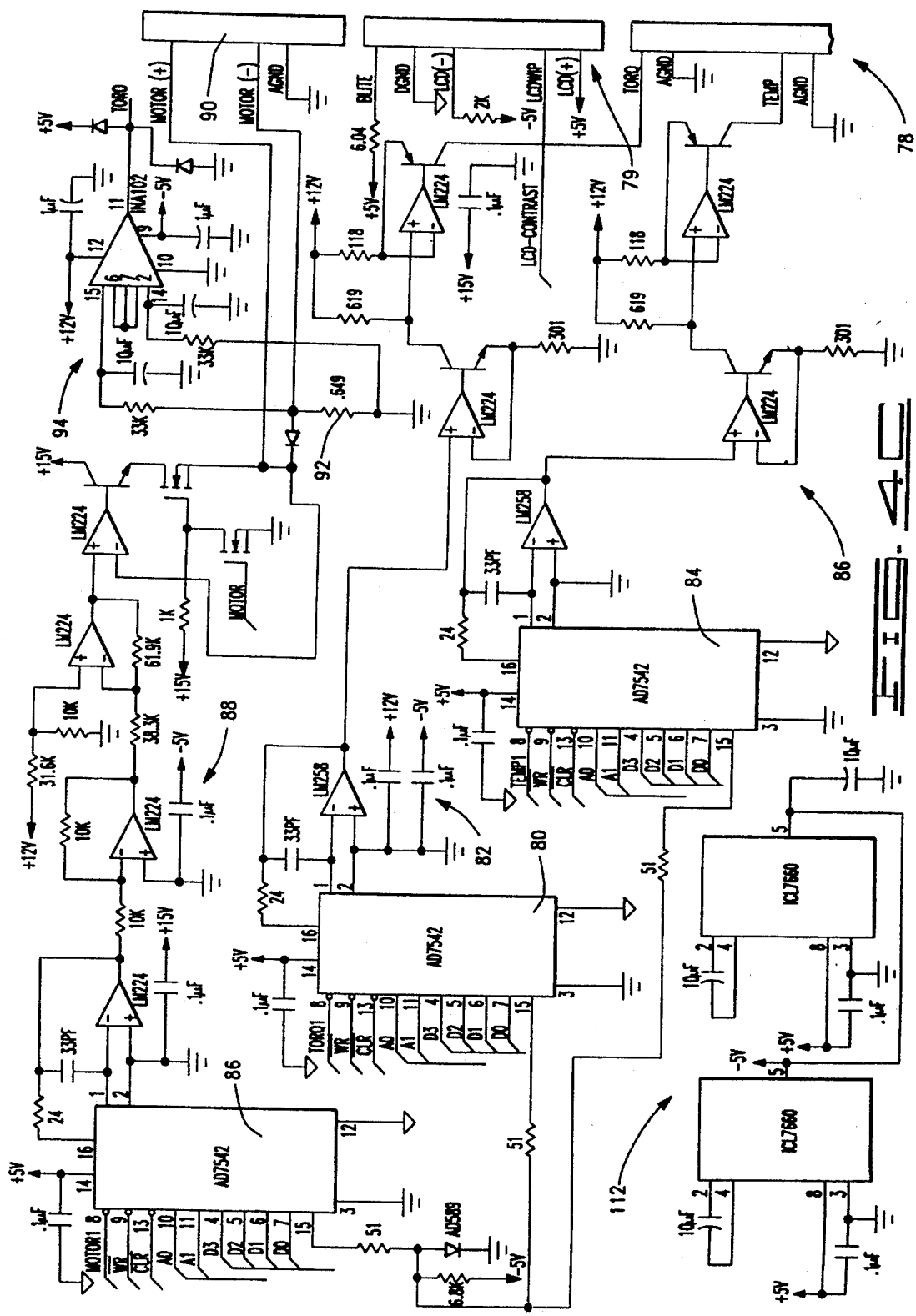

The block diagram of FIG. 1 represents a system that can be used in accordance with the present invention to test a fluid to determine the crosslink time and crosslink temperature. The system comprises a motor 2 with which a speed sensor is associated. The system also comprises a paddle connected by a paddle shaft 4 to the motor 2. A computerized controller 6 controls and records the operation of the system, which system also comprises a vessel 8, or sample cup, to hold the fluid to be tested. The vessel 8 is preferably placed in a heating jacket 10 to bring the fluid to a desired temperature in a prescribed manner. A temperature sensor provides an electrical signal to the controller 6 to monitor the temperature of the fluid sample. The controller 6 has a display 12 and a keypad 14 for data display and entry. The controller 6 contains other analog and digital means for reporting data. The system can also include a carrying case as the preferred embodiment is portable so that it can be hand-carried to an oil or gas well, for example. The foregoing will be further described below with reference to the particular implementations of FIGS. 2–4.

Figure 5:
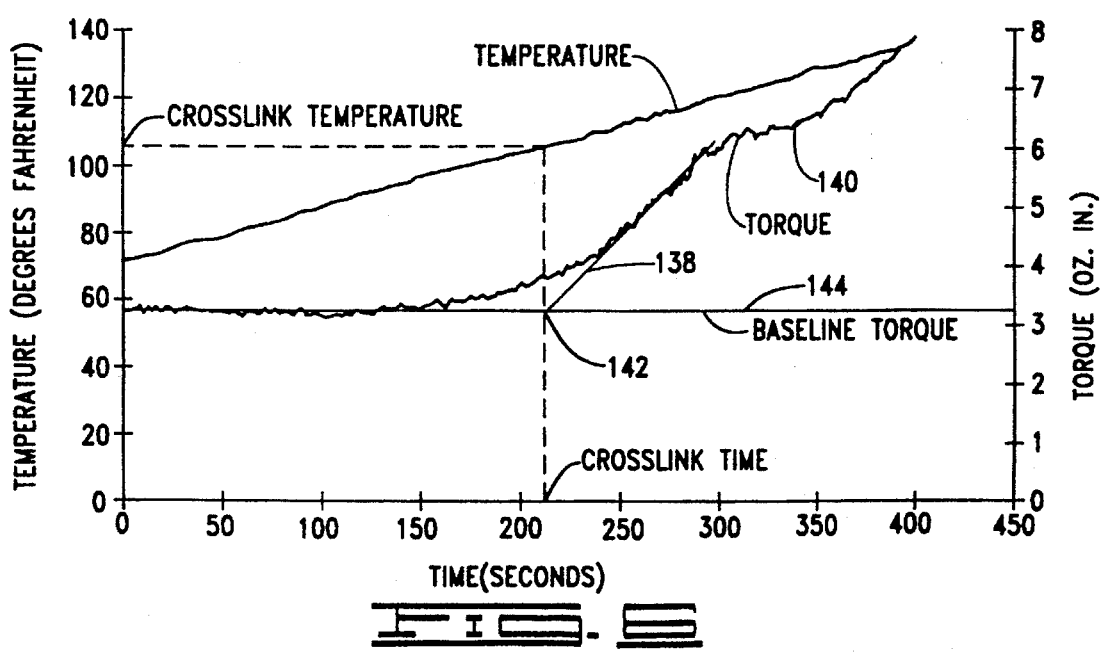
FIGS. 5A and 5B are a flow chart of a program for the controller of FIG. 1 of the preferred embodiment of the present invention.

In use, the paddle is placed in the vessel 8 containing the fluid to be tested. The motor 2 turns the paddle. The paddle is designed to cause drag even on very thin fluids. A baseline value related to the torque of the rotated paddle in the fluid is established after the sample is placed in the test system and the paddle is first rotated. Preferably the fluid sample is concurrently heated along a desired temperature profile (e.g., an increasing temperature ramp). As the fluid thickens due to the effects of time and temperature on the crosslinking agent in the fluid, the controller 6 varies the power to the motor 2 so that the paddle is rotated at a constant rotational speed in the fluid. The increase in powers required to maintain the motor speed at the set speed indicates the crosslink phenomenon (i.e., the power increases proportionally with increasing crosslinking). The crosslink phenomenon is determined in relation to this power increase and the established base line. To do this, the controller 6 automatically uses the fluid sample's torque data, which in the preferred embodiment is defined by the current draw of the motor 2 as energized by the controller 6, to determine crosslink time. The crosslink time is determined by finding the intersection of a line, running through the torque data with the steepest slope as found by linear regression, and the baseline value. A corresponding crosslink temperature is the temperature of the sample at the determined crosslink time. The foregoing will be further described below with reference to FIGS. 5 and 6.

Referring to FIGS. 2 and 3, a particular implementation of the motor and speed sensor 2, vessel 8, heater 10 apparatus will be described. The apparatus includes a base 16 supported by feet 18 such as suitable for sitting on a table top in a laboratory, for example. The vessel 8 is shown in FIGS. 2 and 3 as a sample cup of conventional type. Pins 20 extend from the bottom of the cup 8 to fit into holes defined in the upper surface of the base 16 so that the cup 8 does not rotate during a test.

Surrounding the cup 8 is a heater 22 housed in a heater cover 24 having a slot 26 (FIG. 3) through which pliers 28 extend to clamp the heater 22 around the cup 8. Before the heater 22 is used, a sufficient amount of fluid (e.g., 350 milliliters) should be placed in the cup. A connector 30 (FIG. 3) is attached to the heater cover 24 and provides electrical connections between the heater 22 and a cable from the controller 6. In a particular implementation, the heater 22 is a 120 volt, approximately 1,000 watt band heater switched on and off by a triac (not shown).

The paddle of the particular implementation is shown in phantom in FIG. 2 as a dual ribbon or double helix paddle 32 connected at the lower end of the paddle shaft 4. The upper end of the paddle shaft 4 couples in a paddle chuck 33 rotatably connected to the drive shaft of the motor 2. A double helix paddle is preferred in the particular implementation to provide increased agitation whereby if sand or other particulate matter is contained in the fluid under test it will be maintained in suspension.

The motor 2 is mounted in an enclosure 34 mounted on a motor support plate 36 (FIG. 3). The support plate 36 is attached to a slide 38 which slidably receives a post 40 secured at its lower end to the base 16. The position of the slide 38 along the post 40 is maintained by operation of a screw 42 received through a hole in the slide 38 for releasable engagement against the post 40. The slide 38 can be lifted or lowered once the screw 42 is released by an operator using a handle 44 attached to the slide 38. An electrical connector 46 is attached to the enclosure 34. An electrical cable from the controller 6 connects to the connector 46, and the connector 46 connects to electrical components within the enclosure, specifically the motor and the speed sensor.

In a particular implementation, the motor 2 is a dc servo motor having 12 volt windings. An optical encoder (e.g., a 500 pulses per revolution optical encoder) is included to sense the rotational speed of the motor drive shaft.

In the particular implementation shown in FIGS. 2 and 3, the temperature of the sample fluid in the cup 8 is sensed by a resistance-type temperature detector contained in a tube 48 connected to a tube fitting 49. The sensor portion of the temperature detector is at the lower end of the tube 48 so that it is immersed in the fluid when the subassembly on the slide 38 is suitably lowered. The electrical signal generated by the detector 48 is communicated to the controller 6 through the connector 46 attached to the enclosure 34.

Referring to FIGS. 4A–4C, a particular implementation of the controller 6 will be described.

The controller 6 is operated by a digital computer including a microcontroller chip 50 which operates in response to a program contained in memory chips 52, 54 (EPROM) as shown in FIG. 4A. The computer also includes memory chips 56, 58 shown in FIG. 4B. The memory chip 56 is specifically embodied as an EEPROM which contains instrument calibration data that may need to be changed on occasion but can be easily and readily stored between system use. The memory chip 58 is embodied by a SRAM which provides working and storage space during operation of the computer.

The microcontroller 50 also operates in response to a crystal-based timing circuit 60 and a precision voltage reference circuit 62 (FIG. 4A). The microcontroller 50 has conventional address and data buses. The address bus is made into a 16-bit bus by means of flip-flop chip 64 shown in FIG. 4A. Addressing also occurs in response to chip select signals generated under control of the microcontroller 50 via a demultiplexer/decoder chip 66 (FIG. 4B).

External control of the microcontroller 50 is provided via the keypad 14 shown in FIG. 1 and the keypad interface connector 68 shown in FIG. 4A. External data can also be provided to the microcontroller 50 via RS-232 interface connector and circuit 70 shown in FIG. 4A; however, this receive function is disabled by software in a particular implementation. Data can also be output from the microcontroller 50 via the circuit 70.

Data can be output visually through the display 12 shown in FIG. 1. Operation of the display 12 occurs under control of the microcontroller 50 as provided through a digital output bus 72 shown in FIG. 4B. Data is provided from the microcontroller 50 onto the bus 72 via flip-flop chip 74, and data from the digital output bus 72 to the microcontroller 50 is provided through buffer/line driver chip 76 shown in FIG. 4B other control signals for the display 12 are provided through interface 77 to which the digital output bus is also connected as shown in FIG. 4B, and via interface connector 79 shown in FIG. 4C.

FIG. 4C also shows that two specific analog outputs are provided from the controller 6 at the interface connector 78 in FIG. 4C. These two outputs can be software configured so each can output one of the following signals: crosslink time, crosslink temperature, torque, and fluid temperature. Torque and fluid temperature are illustrated by the labeling at part 78 in FIG. 4C. The analog torque signal is provided by the microcontroller 50 operating a digital to analog converter 80 which drives analog output circuit 82 shown in FIG. 4C. The analog temperature signal is provided by the microcontroller 50 controlling a digital to analog converter 84 which drives an analog output circuit 86 as also shown in FIG. 4C.

Another analog output circuit is shown in FIG. 4C. This provides the analog output for controlling the speed of the motor 2. This circuit includes a digital to analog converter 86 which drives analog output circuit 88 connected to interface connector 90. The connector 90 connects via a cable to the connector 46 on the enclosure 34 housing the motor 2.

The output circuit 88 includes a resistor 92 through which current is sensed by amplifier circuit 94 to provide a torque indicating signal to the microcontroller 50. This is specifically a signal representing or responsive to the current provided to the motor 2 to maintain it at a desired operating speed. This energization signal is proportional to the torque of the motor 2 and its driven paddle, which torque is proportional to viscosity, and thus crosslinking, of the sampled fluid. The signal provided to the microcontroller 50 is specifically an analog voltage which is converted by the microcontroller into a corresponding digital signal stored in the memory 58 as representing a respective sensed torque indicating parameter.

The microcontroller 50 operates the motor drive circuit 86, 88 in response to the sensed speed of rotation of the drive shaft of the motor 2. This is sensed by the sensor included with the aforementioned particular implementation of the motor 2. This sensor's signal is communicated via the connector 46, intervening cable, and interface connector 96 shown in FIG. 4A. The communicated signal is a frequency signal representing speed of rotation. This is compared to a parameter stored in the memory 58 to define a preset desired speed at which the motor drive shaft is to be maintained (on power up, most of the variables stored in memory 56 are transferred to memory 58). If a variation is detected, the microcontroller 50 provides a suitable digital output which is converted through the digital to analog converter 86 to adjust the energization of the motor as referred to above.

The aforementioned torque sensing by monitoring the current through the resistor 92 provides a simpler, more reliable measure of a viscosity proportional characteristic; however, other means can also be used for sensing viscosity. Any accurate torque sensing signal can be used, but any other viscosity proportional parameter can be used as well.

The microcontroller 50 also controls the heater 22 shown in FIG. 2. The microcontroller 50 provides a signal to heater driver circuit 98 which includes an optoisolator triac driver circuit 100 shown in FIG. 4B that operates the triac connected to the heater 22. The resulting temperature is sensed by the temperature detector in the tube 48. The temperature sensor provides its signal through the connector 46, the intervening cable, and interface connector 102 shown in FIG. 4A. The interface 102 connects within the controller 6 to circuit 104 which includes a ten volt reference chip 106 and an amplifier circuit 109 providing an output to the microcontroller 50.

The circuits shown in FIGS. 4A–4C and described above are energized via power circuits 110, 112 shown in FIGS. 4B and 4C, respectively.

Referring to the foregoing equipment and the flow chart shown in FIGS. 5A and 5B, the method of the present invention will be described. During the following explanation, it is to be noted that the microcontroller 50 continually monitors the speed of the motor 2 and controls the motor 2 to maintain the speed at a desired setting. In a particular implementation, the preset desired speed of rotation is 150 revolutions per minute. This is lower than the typically standard 300 revolutions per minute used in other viscosity test systems. It has been determined that 300 revolutions per minus is too high because it thins the fluid too much to measure the viscosity change accurately. A slower speed than 150 revolutions per minute would be desirable, but it may result in particulate material dropping out of suspension in those sample fluids which are mixtures of liquid and solid material.

The microcontroller 50 is also continually obtaining data representing a viscosity proportional parameter (e.g., torque) as well as temperature data. Time data is also maintained in response to the crystal timing circuit 60. In the particular implementation, the time is relative to a reset time. In the particular implementation, a torque related parameter is taken every 0.1 second, and temperature data is recorded every second. Only the latest twelve minutes worth of temperature data is retained in the particular implementation. As to the torque data, although it is taken every 0.1 second, the slope calculations referred to below are determined using only every two second torque data point. This reduces the memory and computing power requirements of the controller 6. Clearly, these are not limitations of the present invention but are details of the particular implementation.

To begin a test for crosslinking of a fluid, a sample of the fluid is placed in the cup 8. This sample has the crosslinking agent in it. The fluid is heated, if desired, by the microcontroller 50 controlling the heater 22 via the circuit 98 (FIG. 4B) and monitoring the temperature via the circuit 104 (FIG. 4A). The microcontroller 50 also controls the motor 2 to rotate the paddle 32 through the fluid in the vessel or cup 8. This includes energizing the motor 2 with the programmed electronic controller 6 via the analog output circuit 88 (FIG. 4C). As mentioned, the electronic controller is programmed for periodically sensing rotational speed of the paddle (specifically the rotational speed of the drive shaft of the motor 2) via the sensor signal received through the interface connector 96 (FIG. 4A) and for changing energization of the motor as needed to maintain a constant rotational speed.

The energization of the motor 2 is sensed by the microcontroller 50 via the resistor 92 and its related circuit 94 shown in FIG. 4C. This sensing occurs at sequential times (e.g., the aforementioned 0.1 second sample rate). The nondigital signal from the resistor 92 is processed by the circuit 94 and converted into a digital signal by the internal analog to digital converter of the particular implementation of the microcontroller 50 shown in FIG. 4A. This creates encoded digital signals defining digital energization data representing sensed energization levels. These data are stored in the digital memory 58 shown in FIG. 4B.

Similarly, the temperature a of the fluid is sensed via the temperature sensor and the interface circuit 104 of FIG. 4A during the sequential times. An internal analog to digital converter, of the microcontroller 50 converts these temperature signals into encoded digital signals defining digital temperature data representing the sensed temperatures at the corresponding sequential times. This data is stored in the memory 58.

Figure 5A:
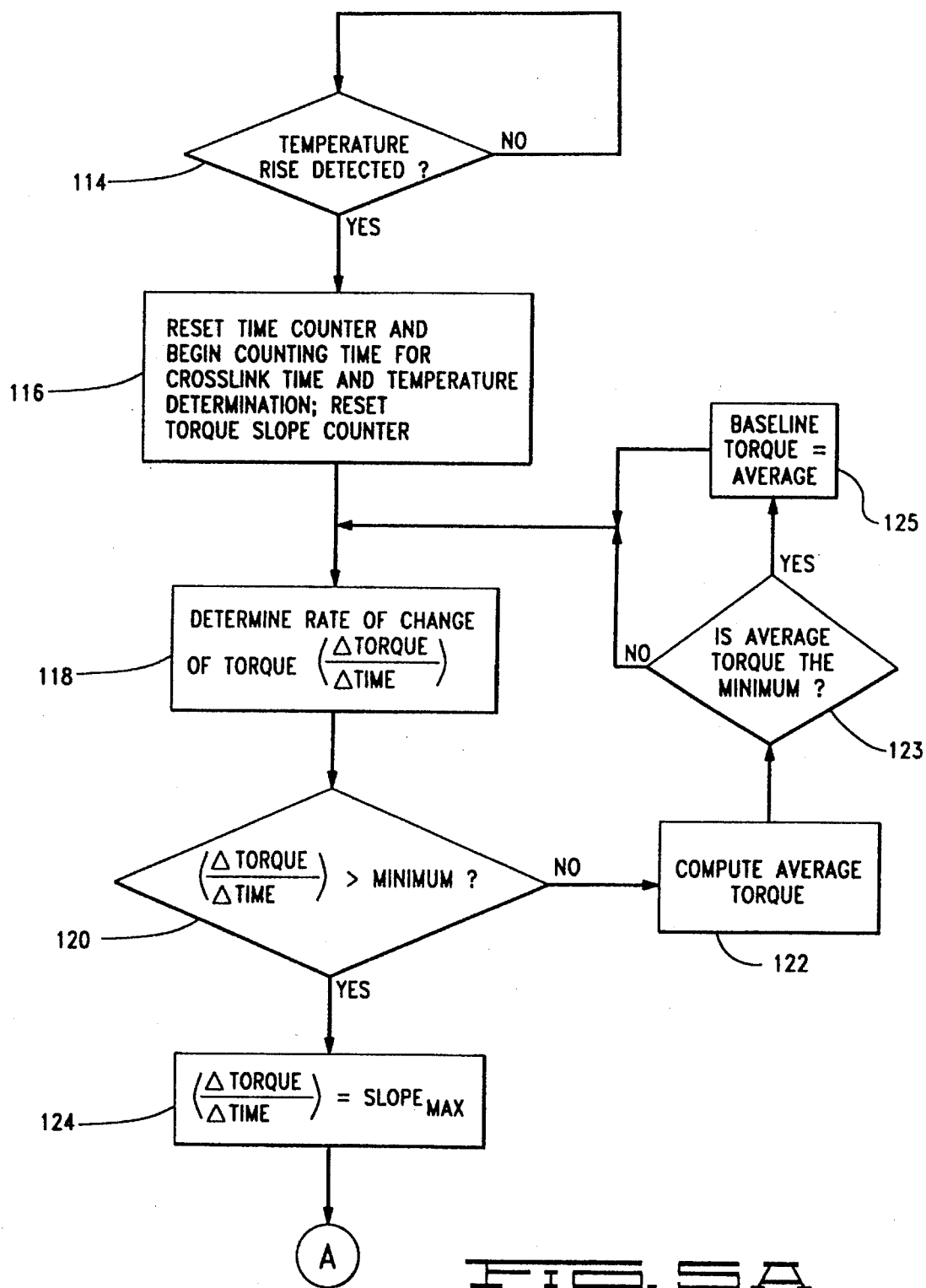

Referring to FIG. 5A, the microcontroller 50 monitors the received and stored temperature data and compares later data to earlier data to determine (such as by subtraction) if a temperature rise above a predetermined threshold has been detected. The threshold varies (increases) with the desired heat rate and is zero for heat rates less than and equal to 5° F./minute. This decision is represented at block 114 in FIG. 5A. Motor control and data acquisition continue before and after such a temperature rise is detected.

When a temperature rise is detected, the microcontroller 50 resets an internally maintained time counter and begins counting time for the crosslink time and temperature determination (in a particular implementation time counting utilizes the time from start-up of the microcontroller, the time from start-up at which reset due to temperature rise occurs, and the known sampling period). Time counting is derived from the timing circuit 60 shown in FIG. 4A. The microcontroller 50 also resets a torque slope counter. This software-implemented counter maintains a count of the number of times a slope determination has been made subsequent to a slope determination considered to be a maximum slope as explained below. These functions are indicated at block 116 in FIG. 5A.

Blocks 118 and 120 of FIG. 5A show that the microcontroller 50 determines when a minimum rate of change of the digital energization data occurs. The flow chart and following explanation refer to the more general parameter torque to which the energization data of the specific implementation is directly related.

This minimum rate of change determination is made in the electronic controller by finding slopes of a curve defined by the torque data points. In a particular implementation, each new slope is found by linear regression on the fifteen current two second data points. Linear regression defines the best fit line through a series of data points in a statistical sense. Linear regression finds a slope and an offset to define a line:

$$\text{slope} = \frac{n \sum_{i=1}^{15} x_i y_i - \sum_{i=1}^{15} x_i \sum_{i=1}^{15} y_i}{n \sum_{i=1}^{15} x_i^2 - \left(\sum_{i=1}^{15} x_i\right)^2}$$

$$\text{offset} = \frac{\sum_{i=1}^{15} y_i \sum_{i=1}^{15} x_i^2 - \sum_{i=1}^{15} x_i \sum_{i=1}^{15} x_i y_i}{n \sum_{i=1}^{15} x_i^2 - \left(\sum_{i=1}^{15} x_i\right)^2}$$

where n=the number of data points (15)

x=time data point y=torque data point

This computation shows the rate of change of the torque as the fluid is heated and crosslinking occurs. Until this slope is a minimum, the rate of change is simply calculated periodically and monitored. The average of the torque data during this period is computed and the minimum torque found is used to define a baseline torque value. In the particular implementation, a baseline energization value is obtained by computing or otherwise determining an average of the digital energization data over a time period between the steps of determining when a temperature rise first occurs and when a minimum rate of change, or slope, of the digital energization data occurs. In the particular implementation this specifically includes using the fifteen point linear regression data pertinent to torque to determine an average at each two second calculation interval. This process is represented by blocks 118, 120, 122, 123, 125 in FIG. 5A. Although not shown in the drawings, in the particular implementation the method continues to look for a baseline energization value even after a minimum slope is detected. This is done by also performing operations 122, 123, 125 prior to block 126 described below with reference to FIG. 5B.

When a calculated actual slope exceeds the preset minimum slope, that actual slope is set as a software-defined maximum slope parameter shown in block 124 of FIG. 5A as "$\text{SLOPE}_{MAX}$". This can be referred to initially as an interim maximum slope because when first set, it is not known whether this particular actual slope value is the ultimate maximum to be used in the invention as explained below.

Figure 5B:
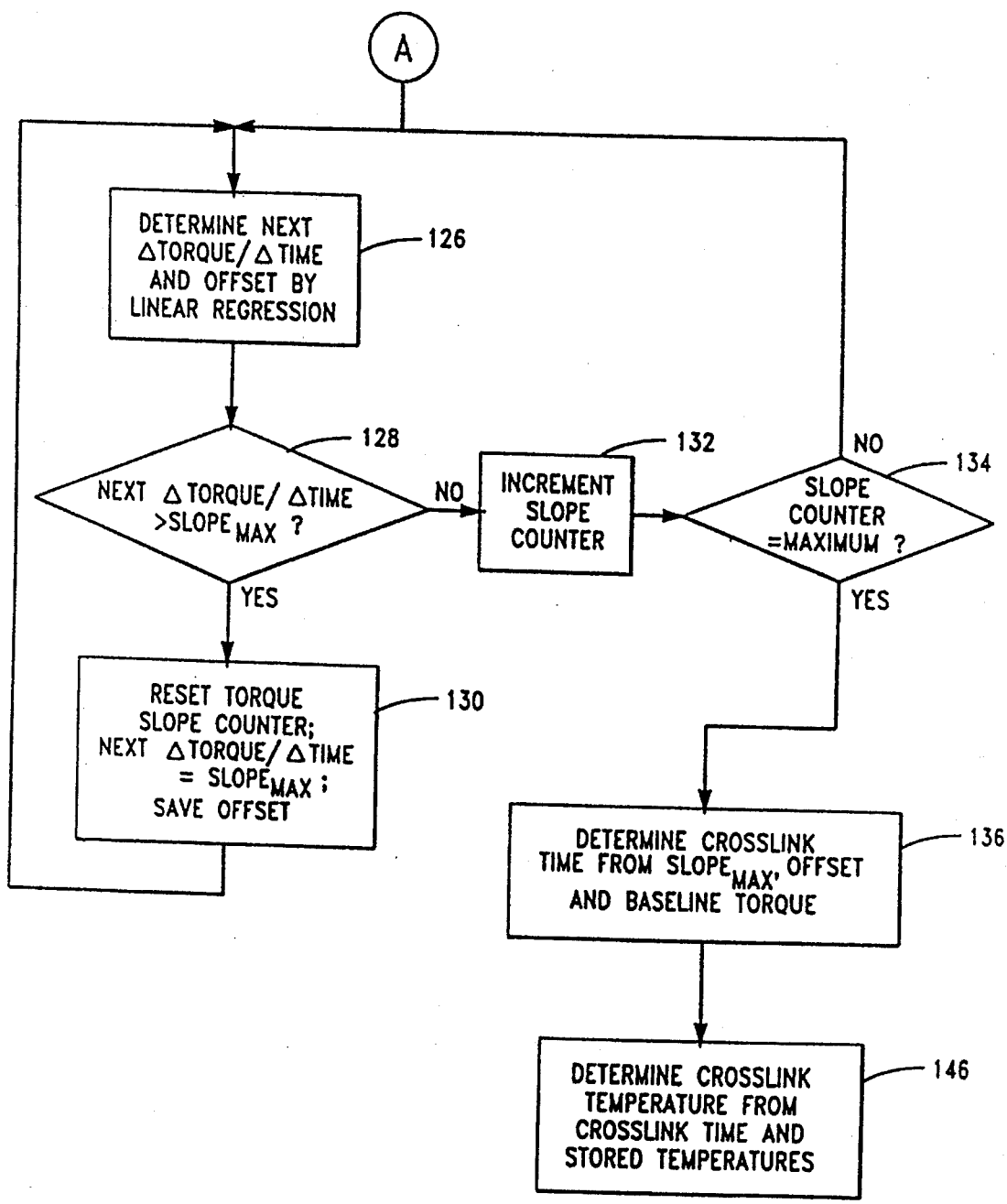

Once an initial interim maximum slope has been defined, the next slope computation is made as indicated at block 126 in FIG. 5B. The microcontroller 50 compares this next slope value with $\text{SLOPE}_{MAX}$ to determine whether this next slope value is greater than the previously defined maximum slope. This is shown at block 128 in FIG. 5B. If the next slope value is greater than the then existing $\text{SLOPE}_{MAX}$, the torque slope counter is reset and such next slope value then becomes the next interim maximum slope to be tested as shown at block 130 in FIG. 5B. This repeats until the next slope calculation is not greater than the then defined interim maximum slope.

When the next slope is not greater than the previously defined maximum slope, the torque slope counter is incremented by the microcontroller 50 and the count in the counter is compared to a predetermined maximum (e.g., 30). This is shown at blocks 132, 134 of FIG. 5B. If the maximum has not been reached, slope computations and comparisons continue (blocks 126, 128) with either the slope counter being incremented (blocks 132, 134) or new interim maximum slopes being defined (block 130).

If an interim maximum slope has been defined and no greater slope is detected within the subsequent maximum number of slope calculations, the microcontroller 50 is programmed to use this last defined interim maximum slope as the actual maximum slope of the energization data curve. Once this ultimate maximum slope has been defined, the microcontroller 50 determines the crosslink time from the maximum slope, its corresponding offset, and the baseline torque as shown at block 136 in FIG. 5B. In the particular implementation, the line of the maximum slope of the curve defined by the torque data is effectively extrapolated back to the point at which the line intersects the baseline value. This is graphically represented in FIG. 6. A line 138 is the line containing the maximum slope of torque curve 140 obtained from the motor energization data. The line 138 extends to a point of intersection 142 with the torque base line 144 as shown in FIG. 6. In actually using the microcontroller 50, the maximum slope and offset will have been defined Coy linear regression and the foregoing steps explained above. The crosslink time is then found from the maximum slope and offset and the basic equation of a line, y=mx+b, where m is the slope, b is the offset and y is the baseline torque. So, x=crosslink time=(y−b)/m.

Once the crosslink time has been determined, the crosslink temperature can be determined by looking up the stored temperature data for the corresponding time. If the crosslink time is not a specific corresponding time data point at which a temperature has been measured, the crosslink temperature can be determined by interpolating between the two adjacent temperature and time points on either side of the crosslink time. This temperature determination is indicated at block 146 in FIG. 5B and is graphically represented in FIG. 6.

Once the crosslink time and temperature have been determined, the microcontroller 50 operates the display 12 via interface connectors 77, 79 in FIGS. 4B and 4C to display these values. In this way, the operator can obtain data for comparing different crosslinked fluids and different temperature effects on the same type of crosslinked fluid.

A particular embodiment of a program for implementing the present invention described above is listed below before the claims.

Thus, the present invention is well adapted to carry out the objects and attain the ends and advantages mentioned above as well as those inherent therein. While a preferred embodiment of the invention has been described for the purpose of this disclosure, changes in the construction and arrangement of parts and the performance of steps can be made by those skilled in the art, which changes are encompassed within the spirit of this invention as defined by the appended claims.

```
/*
    XLINK.C contains main(), menus, initialization of variables,
    and rate up and rate down controls.

*/ include <stdio.h>
include <ctype.h>
#include "reg552.h"
#include "xdef.h"
#include "lcdef.h"

#define one (bit) 1
define DEG (char)0xdf extern idata unsigned long time, tsetpt;
extern idata unsigned int pb1, ib1, setpoint1, t2comp0,
        pb2, ib2, pb3, ib3, adc[], arate, ratesp;
extern idata unsigned char feedforward2, count5sec, pwmcount,
        deltatemp;
extern idata bit manualmo, hibit, lobit, in_flag, keypress,
        manualht, kflag, rbit, rampflag, controlflag,
        xlinksflag, xlinkeflag, const_temp, calcflag, pointflag;
extern idata char loop;
extern idata int v2;

extern xdata unsigned char kcountu, kcountd, skiptime, index, nocounts,
        scounts, pulse2;
extern xdata char ascii_in, newkey, keybuffer[15];
extern xdata unsigned int temperature, ones[10], deltarate, *tempptr,
        xthresh;
extern xdata long offset_time, stemp_ao, timehold, timeh1, sumx, sumy;
extern xdata float xtemp, xtime, xslope, xdiv, xoffset, mslope, sumxy,
        sumx_2;
extern xdata int error_rpm, storq_ao, otorq_ao, otemp_ao;

idata bit mains, lcd_notserial, slopeflag, manmoop, manualao;
xdata unsigned int rpm_setpt, adac, heatpulse, zadc, sadc,
        compadc, motorout, loopcheck, loopcheck1[5], torq2outoff, torq2outrng, temp2outoff,
        temp2outrng;
xdata float speed, faren, rate, max_hrate, nlc, torque,
        tempsp, toffset, tslope, ztemp, stemp, maxtemp, ffwdm, mslp,
        start_temp, vtp, dhrate, bht;
xdata unsigned long time_s, time_t;
xdata unsigned char loop3, pwm_0_20, pwm_0_4, pwm_1_20,
        pwm_1_4, placeptr, aindex[2];

void init(void);
void main(void);
extern void serial_data(void);
extern void write_eeprom (char *value, char *addr, int bytes);
extern void read_eeprom (char *value, char *addr, int bytes);
extern void write_lcd(char info, bit rs);
extern void lcd_init(void);
void cal_init(void);
void menu(void);
void motor_control(void);
void heater_control(void);
void analog_signals(void);
void heater_pid(void);
void item(char *, char *, char *);
/* extern void logo(void); */
extern void dacout(void);
extern void lastline(void);
extern void getinput(void);
void find_toffset(void);
```

```
void find_tslope(void);
void cal_temp(void);
void start_heat(void);
void enter_heat_rate(void);
void enter_max_temp(void);
void enter_max_heat_rate(void);
void set_outputs(void);
void find_torq_val(void);
void find_temp_val(void);
void crosslink_data(void);
void motor_pi(void);
void job_parms(void);
void heat_control(void);
void setup_temp_outputs(void);
void setup_torq_outputs(void);
void set_var(unsigned int channel);
void set_channel(void);
void lut_menu(void);
void reload_default_table(void);
float find_mhrt(char entry, char gw, float sandc);

code struct lut_entry default_table[6] = {
        "Fracgel       \0", 30, 50, 37.12, 42.66, 46.17, 36.88, 42.70, 49.32, 0.0, 5.0, 15.0,
        "Hybor G       \0", 30, 50, 39.47, 42.90, 47.29, 38.39, 43.92, 47.87, 0.0, 5.0, 15.0,
        "MY-T-GEL HT   \0", 30, 50, 40.37, 41.89, 46.89, 40.00, 40.82, 44.88, 0.0, 5.0, 15.0,
        "PUR-GEL III HT\0", 30, 50, 39.20, 43.12, 45.77, 36.88, 41.91, 48.80, 0.0, 5.0, 15.0,
        "Thermagel     \0", 40, 70, 37.00, 41.42, 45.05, 33.50, 37.84, 48.75, 0.0, 5.0, 15.0,
        "VERSGEL HT    \0", 30, 50, 42.42, 46.17, 49.56, 35.55, 41.01, 47.09, 0.0, 5.0, 15.0};

/*
        main() updates the LCD display 4 times per second.
        Calls the initialization routines.
        Controls the rate up rate down features for the manual
        control of outputs.
*/ void main(void)
{
    code char string1[] = "ON ", string2[] = "OFF";
    xdata char* sptr;
    xdata long rttime;

time = 0L;
    in_flag = 0;
    mains = one;
    init();
    while(time < 5L);
    cal_init();
    lcd_init();
    tsetpt = 0;
    while (!tsetpt) {
        if (time > 200L)
            tsetpt = ((unsigned long) temperature) << 7;
    }
    time = 0L;
    offset_time = 0L;
    time_s = 99L;
    time_t = 125L;
    loopcheck = 0;
    while(1) {
        serial_data();
        if ( (time > time_t)) {
            switch (loop3) {
                case 0:
                    rttime = time - offset_time;
                    row1();
                    printf("%5.2foz-in   %2bu:%04.1f", torque,
                            (unsigned char) (rttime / 6000), (rttime %
                            6000) / 100.0);
                    break;
                case 1:
                    if (manualht)
```

```
                                sptr = string2;
                        else
                                sptr = string1;
                        row2();
                        printf("%5.1f%cF    SP:%5.1f%cF", faren, DEG, tempsp,
                                DEG);
                        break;
                case 2:
                        row3();
                        printf("TIME    XLINK    TEMP.");
                        break;
                case 3:
                        if (manualht)
                                sptr = string2;
                        else
                                sptr = string1;
                        rttime = (long) (xtime * 100.0);
                        row4();
                        printf("%2bu:%04.1f  %s", (unsigned char)
                                    (rttime / 6000), (rttime %6000) / 100.0,
                                    sptr);
                        printf(" %5.1f%cF", xtemp, DEG);
                        break;
                default:
                        break;
                }
           loop3++;
           if (loop3 > 3)
                loop3 = 0;
           time_t = time + 25L;
           }
    if (keypress) {
           switch (newkey) {
                case 'A':
                        keypress = 0;
                        menu();
                        break;
                case 'B':
                        keypress = 0;
                        enter_heat_rate();
                        break;
                case 'C':
                        keypress = 0;
                        enter_max_temp();
                        break;
                case 'F':
                        keypress = 0;
                        enter_max_heat_rate();
                        break;
                case 'G':
                        keypress = 0;
                        if (!manualht) {
                                manualht = one;
                                pulse2 = 0;
                                manualmo = one;
                                P4 |= 0x04;
                                }
                        else
                                start_heat();
                        break;
                default:
                        break;
                }
           }
    loopcheck++;
    }
}

/*
    menu() is the entry to the menu system.
*/ void menu(void)
```

```
{
char choice;

choice = 0;
mains = 0;
item("1. Motor Control", "2. Heater Control", "3. Analog Signals");
while (!choice) {
    row4();
    printf("4. Look up table");
    write_lcd(0x0e, 0);
    write_lcd(0xe7, 0);
    choice = _getkey();
    switch(choice) {
        case '1':
            motor_control();
            break;
        case '2':
            heater_control();
            break;
        case '3':
            analog_signals();
            break;
        case '4':
            lut_menu();
            break;
        case 'A':
            break;
        default:
            choice = 0;
            break;
    }
}
write_lcd(0x0c, 0);
mains = one;
} void lut_menu(void)
{
    char choice, response, sc_ptr, gw_ptr, entry_ptr;
    xdata unsigned char ctemp;
    int errr;
    float ftemp, ftemp2;
    xdata char *tptr;
    xdata unsigned int poff;

choice = 0;
    response = 0;
    write_lcd(0x01, 0);
    row1();
    printf("1. Enter heat rate");
    row2();
    printf("2. Default Table");
    row3();
    printf("3. View/Edit Table");
    while (!choice) {
        write_lcd(0x0e, 0);
        row4();
        printf("4. Crosslink Data");
        write_lcd(0xe7, 0);
        choice = _getkey();
        switch(choice) {
            case '1':
                enter_max_heat_rate();
                break;
            case '2':
                write_eeprom((char *) default_table, (char *) lut_ptr, 324);
                break;
            case '3':
                item("Enter for next", "1 to quit",
                        "2 to edit");
                response = _getkey();
                if (response == 0x0d || response == '2') {
                    gw_ptr = 0;
                    sc_ptr = 0;
```

```
entry_ptr = 0;
do {
    write_lcd(0x01, 0);
    row1();
    printf("%2bu. %s", (entry_ptr+1),
            lut_ptr[entry_ptr].label);
    row2();
    printf("Gel weight: %bu lb.",
            lut_ptr[entry_ptr].gelw[gw_ptr]);
    row3();
    printf("%4.1f lb/gal sand",
            lut_ptr[entry_ptr].scon[sc_ptr]);
    row4();
    printf("%5.2f %cF/min",
            lut_ptr[entry_ptr].mhrt[gw_ptr][sc_ptr],
            DEG);
    write_lcd(0xe7, 0);
    response = _getkey();
    if (response == '2') {
        do {
            write_lcd(0x01, 0);
            row1();
            printf("Enter the gel weight");
            row2();
            printf("[%2bu lbs.]:",
                    lut_ptr[entry_ptr].gelw[gw_ptr]);
            write_lcd(0xe0, 0);
            getinput();
        } while(keybuffer[0] != '\0' && ((errr =
                sscanf(keybuffer, "%bu", &ctemp)) == 0
                || errr == EOF));
        if (keybuffer[0] != '\0' && ctemp > 5 &&
                ctemp < 200)
            write_eeprom(&ctemp, (char *)
                    &lut_ptr[entry_ptr].gelw[gw_ptr], 1);
        do {
            write_lcd(0x01, 0);
            row1();
            printf("Enter the heat rate");
            row2();
            printf("[%5.2f %cF/min.]:",
                    lut_ptr[entry_ptr].mhrt[gw_ptr][sc_ptr], DEG);
            write_lcd(0xe0, 0);
            getinput();
        } while(keybuffer[0] != '\0' && ((errr =
                sscanf(keybuffer, "%f", &ftemp)) == 0
                || errr == EOF));
        if (keybuffer[0] != '\0' && ftemp > 15.00 &&
                ftemp < 75.00)
            write_eeprom((char *) &ftemp, (char *)
                    &lut_ptr[entry_ptr].mhrt[gw_ptr][sc_ptr], 4);
        do {
            write_lcd(0x01, 0);
            row1();
            printf("Enter the sand");
            row2();
            printf("concentration");
            row3();
            printf("[%4.1f lb./gal.]:",
                    lut_ptr[entry_ptr].scon[sc_ptr]);
            write_lcd(0xe0, 0);
            getinput();
        } while(keybuffer[0] != '\0' && ((errr =
                sscanf(keybuffer, "%f", &ftemp)) == 0
                || errr == EOF));
        if (keybuffer[0] != '\0' && ftemp >= 0.0 &&
                ftemp < 32.0)
            write_eeprom((char *) &ftemp, (char *)
                    &lut_ptr[entry_ptr].scon[sc_ptr], 4);
    }
    else {
        sc_ptr++;
        if (sc_ptr > 2) {
            sc_ptr = 0;
            gw_ptr++;
```

```
                                    if (gw_ptr > 1) {
                                        gw_ptr = 0;
                                        entry_ptr++;
                                        if (entry_ptr > 5) {
                                            response = '1';
                                        }
                                    }
                                }
                            } while (response == 0x0d ||
                                response == '2');
                        }
                        break;
                    case '4':
                        crosslink_data();
                        break;
                    case 'A':
                        break;
                    default:
                        choice = 0;
                        break;
                }
            }
        } float find_mhrt(char entry, char gw, float sandc)
        {
            if (sandc <= lut_ptr[entry].scon[0])
                sandc = lut_ptr[entry].mhrt[gw][0];
            else if (sandc >= lut_ptr[entry].scon[2])
                sandc = lut_ptr[entry].mhrt[gw][2];
            else if (sandc <= lut_ptr[entry].scon[1])
                sandc = (sandc - lut_ptr[entry].scon[0])/(lut_ptr[entry].scon[1] - lut_ptr[entry].scon[0]) *
                        (lut_ptr[entry].mhrt[gw][1] - lut_ptr[entry].mhrt[gw][0]) +
                        lut_ptr[entry].mhrt[gw][0];
            else
                sandc = (sandc - lut_ptr[entry].scon[1])/(lut_ptr[entry].scon[2] - lut_ptr[entry].scon[1]) *
                        (lut_ptr[entry].mhrt[gw][2] - lut_ptr[entry].mhrt[gw][1]) +
                        lut_ptr[entry].mhrt[gw][1];
            return(sandc);
        } void crosslink_data(void)
        {
            char choice;
            int errr;

choice = 0;
            write_lcd(0x01, 0);
            row1();
            printf("1. OVS = %2bu", scounts);
            row2();
            printf("2. %1bu points skipped", skiptime);
            row3();
            printf("3. MSLP = %6.5f", mslp);
            while (!choice) {
                write_lcd(0x0e, 0);
                write_lcd(0xe7, 0);
                choice = _getkey();
                switch(choice) {
                    case '1':
                        item("Enter the number", "of low slopes",
                                "to overshoot");
                        do {
                            lastline();
                            getinput();
                        } while ((errr = sscanf(keybuffer, "%bu", &scounts))
                                == EOF || errr == 0);
                        write_eeprom((char *) &scounts, sc_back, 1);
                        break;
                    case '2':
                        item("Enter the number", "of data points", "to skip:");
                        do {
```

```
                        lastline();
                        getinput();
                    } while ((errr = sscanf(keybuffer, "%bu", &skiptime))
                            == 0 || errr == EOF);
                    break;
                case '3':
                    item("Enter the ", "minimum slope", "to compare:");
                    do {
                        lastline();
                        getinput();
                    } while ((errr = sscanf(keybuffer, "%f", &mslp)) ==
                            0 || errr == EOF);
                    write_eeprom((char *) &mslp, mslp_back, 4);
                    mslope = mslp;
                    slopeflag = 0;
                    break;
                case '4':
                    write_lcd(0x01, 0);
                    row1();
                    printf("%bu  %bu", nocounts, scounts);
                    row2();
                    printf("%bu", index);
                    row3();
                    printf("%12.10f", mslope);
                    row4();
                    printf("%12.10f", xslope);
                    _getkey();
                    write_lcd(0x01, 0);
                    row1();
                    printf("%ld", timehold);
                    row2();
                    printf("%ld", timeh1);
                    row3();
                    printf("%-11.3f", xoffset);
                    row4();
                    printf("%6u", xthresh);
                    _getkey();
                    write_lcd(0x01, 0);
                    row1();
                    printf("%u  %u", loopcheck1[0], loopcheck1[1]);
                    row2();
                    printf("%u  %u", loopcheck1[2], loopcheck1[3]);
                    row3();
                    printf("%u", loopcheck1[4]);
                    _getkey();
                    loopcheck1[0] = 0;
                    loopcheck1[1] = 0;
                    loopcheck1[2] = 0;
                    loopcheck1[3] = 0;
                    loopcheck1[4] = 0;
                    break;
                case 'A':
                    break;
                default:
                    choice = 0;
                    break;
            }
        }
    }

/*
        motor_control() is the entry to the functions and calibration
        for the control of the dc motor.
    */ void motor_control(void)
{
    char choice;
    int errr;

choice = 0;
    write_lcd(0x01, 0);
    row1();
```

```c
        printf("1. PI and Set Point");
        row2();
        printf("2. Cal NLC");
        row3();
        printf("3. NLC = %5.3f", nlc);
        while (!choice) {
            row4();
            printf("4. Set motor output");
            write_lcd(0x0e, 0);
            write_lcd(0xe7, 0);
            choice = _getkey();
            switch(choice) {
                case '1':
                    motor_pi();
                    break;
                case '2':
                    nlc = (float) adc[4] * TORQUE_COUNTS;
                    write_eeprom((char *) &nlc, nlc_back, 4);
                    break;
                case '3':
                    item("Enter the no load", "current for the",
                            "motor (amps):");
                    do {
                        lastline();
                        getinput();
                    } while ((errr = sscanf(keybuffer, "%f",
                                    &nlc)) == 0 || errr == EOF);
                    write_eeprom((char *) &nlc, nlc_back, 4);
                    break;
                case '4':
                    item("Enter the output", "counts to the",
                            "motor (0-4095)");
                    do {
                        lastline();
                        getinput();
                    } while ((errr = sscanf(keybuffer, "%u", &motorout))
                            == 0 || errr == EOF);
                    if (motorout > 4095)
                        motorout = 4095;
                    manmoop = one;
                    manualmo = one;
                    P4 &= 0xfb;
                    break;
                case 'A':
                    break;
                default:
                    choice = 0;
                    break;
            }
            setup_torq_outputs();
        }
    } void setup_torq_outputs()
    {
    torq2outoff = ((unsigned int) (nlc / TORQUE_COUNTS));
    torq2outrng = ((unsigned int) (((20.0 / TORQUE_GEAR) + nlc) / TORQUE_COUNTS)) - torq2outoff;
    } void setup_temp_outputs()
    {
    temp2outoff = ((unsigned int) (32.0 - toffset) / tslope);
    temp2outrng = ((unsigned int) ((212 - toffset) / tslope)) - temp2outoff;
    } void motor_pi(void)
    {
    char choice;
    int errr;

choice = 0;
    write_lcd(0x01, 0);
```

```
    row1();
    printf("1. PB1 = %2u", pb1);
    row2();
    printf("2. IB1 = %2u", ib1);
    row3();
    printf("3. STPT = %3u", rpm_setpt);
    while (!choice) {
        write_lcd(0x0e, 0);
        write_lcd(0xe7, 0);
        choice = _getkey();
        switch(choice) {
            case '1':
                item( "Enter the propor-", "tional gain for",
                        "the motor:");
                do {
                    lastline();
                    getinput();
                } while ((errr = sscanf(keybuffer, "%u", &pb1)) ==
                        EOF || errr == 0);
                write_eeprom((char *) &pb1, pb1_back, 2);
                break;
            case '2':
                item("Enter the inverse", "reset time for", "the motor");
                do {
                    lastline();
                    getinput();
                } while ((errr = sscanf(keybuffer, "%u", &ib1)) ==
                        0 || errr == EOF);
                write_eeprom((char *) &ib1, ib1_back, 2);
                break;
            case '3':
                item("Enter the motor", "speed set point", "(rpm):");
                do {
                    lastline();
                    getinput();
                } while ((errr = sscanf(keybuffer, "%u",
                        &rpm_setpt)) == EOF || errr == 0);
                write_eeprom((char *) &rpm_setpt, rpm_back, 2);
                setpoint1 = (int) (rpm_setpt/ RPM_CONST);
                error_rpm = (int) (.9 * setpoint1);
                break;
            case 'A':
                break;
            default:
                choice = 0;
                break;
        }
    }
}

/*
    heater_control() is the menu for the heat ramp setup and start.
*/ void heater_control(void)
{
    int errr;
    char choice;

choice = 0;
    write_lcd(0x01, 0);
    row1();
    printf("1. PI Setup");
    row2();
    printf("2. Heat Control");
    row3();
    printf("3. Job Parameters");
    while (!choice) {
        write_lcd(0x0e, 0);
        row4();
        printf("4. Settings");
        write_lcd(0xe7, 0);
        choice = _getkey();
```

```c
                    switch(choice) {
                        case '1':
                            heater_pid();
                            break;
                        case '2':
                            heat_control();
                            break;
                        case '3':
                            job_parms();
                            break;
                        case '4':
                            write_lcd(0x01, 0);
                            row1();
                            printf("Rate:     %4.1f%cF/min", rate, DEG);
                            row2();
                            printf("Max Rate: %4.1f%cF/min", max_hrate, DEG);
                            row3();
                            printf("Max Temp.: %5.1f%cF", maxtemp, DEG);
                            write_lcd(0xe7, 0);
                            _getkey();
                            break;
                        case 'A':
                            break;
                        default:
                            choice = 0;
                            break;
                    }
                }
        } void heat_control (void)
{
    int errr;
    char choice;

choice = 0;
    write_lcd(0x01, 0);
    row1();
    printf("1. PWM2 = %3bu", pulse2);
    row2();
    printf("2. FFWDM = %4.2f", ffwdm);
    while (!choice) {
        write_lcd(0x0e, 0);
        write_lcd(0xe7, 0);
        choice = _getkey();
        switch(choice) {
            case '1':
                item("Set the heater", "output manually" , "(0-100):");
                do {
                    lastline();
                    getinput();
                } while ((errr = sscanf(keybuffer, "%bu", &pulse2))
                            == 0 || errr == EOF);
                manualht = one;
                break;
            case '2':
                item("Enter the multiplier", "for the heater",
                        "feedforward term:");
                do {
                    lastline();
                    getinput();
                } while ((errr = sscanf(keybuffer, "%f", &ffwdm)) ==
                            0 || errr == EOF);
                write_eeprom((char *) &ffwdm, ffwdm_back, 4);
                break;
            case 'A':
                break;
            default:
                choice = 0;
                break;
        }
    }
}
```

```c
void job_parms (void)
{
    int errr;
    char choice;

choice = 0;
    write_lcd(0x01, 0);
    row1();
    printf("1. BHT = %5.1f%cF", bht, DEG);
    row2();
    printf("2. Vol. = %6.0f gal", vtp);
    row3();
    printf("3. Rate = %5.1f bpm", dhrate);
    while (!choice) {
        write_lcd(0x0e, 0);
        row4();
        printf("4. Gel Temp= %5.1f%cF", start_temp, DEG);
        write_lcd(0xe7, 0);
        choice = _getkey();
        switch(choice) {
            case '1':
                item("Enter bottom hole", "temperature in" ,
                        "degrees Fahrenheit:");
                do {
                    lastline();
                    getinput();
                } while ((errr = sscanf(keybuffer, "%f", &bht))
                        == 0 || errr == EOF);
                write_eeprom((char *) &bht, bht_back, 4);
                break;
            case '2':
                item("Enter volume to", "perforations in" , "gallons:");
                do {
                    lastline();
                    getinput();
                } while ((errr = sscanf(keybuffer, "%f", &vtp))
                        == 0 || errr == EOF);
                write_eeprom((char *) &vtp, vtp_back, 4);
                break;
            case '3':
                item("Enter the downhole", "rate in bpm:",
                        "");
                do {
                    lastline();
                    getinput();
                } while ((errr = sscanf(keybuffer, "%f", &dhrate)) ==
                        0 || errr == EOF);
                write_eeprom((char *) &dhrate, bpm_back, 4);
                break;
            case '4':
                item("Enter the gel's", "beginning temp.",
                        "if Farhenheit:");
                do {
                    lastline();
                    getinput();
                } while ((errr = sscanf(keybuffer, "%f", &start_temp)) ==
                        0 || errr == EOF);
                write_eeprom((char *) &start_temp, stt_back, 4);
                break;
            case 'A':
                break;
            default:
                choice = 0;
                break;
        }
        rate = (bht - start_temp)/(vtp/(dhrate * 42.0));
    }
}

/*
    heat_pid() allows for the entry of pid parameters for the
    control of the heater.
*/
```

```c
void heater_pid(void)
{
    int errr, ptemp;
    char choice;

choice = 0;
    write_lcd(0x01, 0);
    row1();
    printf("1. PB2 = %3u", pb2);
    row2();
    printf("2. IB2 = %2u", ib2);
    row3();
    printf("3. PB3 = %2u", pb3);
    while (!choice) {
        write_lcd(0x0e, 0);
        row4();
        printf("4. IB3 = %2u", ib3);
        write_lcd(0xe7, 0);
        choice = _getkey();
        switch(choice) {
            case '1':
                item("Enter the propor-", "tional gain for the",
                        "temperature error:");
                do {
                    lastline();
                    getinput();
                    } while((errr = sscanf(keybuffer, "%u", &pb2)) ==
                            0 || errr == EOF);
                write_eeprom((char *) &pb2, pb2_back, 2);
                break;
            case '2':
                item("Enter the inverse", "reset time for the",
                        "temperature error");
                do {
                    lastline();
                    getinput();
                    } while ((errr = sscanf(keybuffer, "%u", &ib2)) ==
                            0 || errr == EOF);
                write_eeprom((char *) &ib2, ib2_back, 2);
                break;
            case '3':
                item("Enter the propor-", "tional gain for the",
                        "heat rate error:");
                do {
                    lastline();
                    getinput();
                    } while((errr = sscanf(keybuffer, "%u", &pb3)) ==
                            0 || errr == EOF);
                write_eeprom((char *) &pb3, pb3_back, 2);
                break;
            case '4':
                item("Enter the inverse", "reset time for the",
                        "heat rate error");
                do {
                    lastline();
                    getinput();
                    } while ((errr = sscanf(keybuffer, "%u", &ib3)) ==
                            0 || errr == EOF);
                write_eeprom((char *) &ib3, ib3_back, 2);
                break;
            case 'A':
                break;
            default:
                choice = 0;
                break;
        }
    }
}

/*
    analog_signals will allow entry of calibration information for
    the torque and temperature analog outputs.
```

```
*/ void analog_signals(void)
{
    char choice;
    int errr;

choice = 0;
    write_lcd(0x01, 0);
    row1();
    printf("1. Temperature probe");
    row2();
    printf("2. Set analog outs");
    row3();
    printf("3. Set torque range");
    while (!choice) {
        write_lcd(0x0e, 0);
        row4();
        printf("4. Assign outputs");
        write_lcd(0xe7, 0);
        choice = _getkey();
        switch(choice) {
            case '1':
                cal_temp();
                break;
            case '2':
                set_outputs();
                break;
            case '3':
                find_torq_val();
                break;
            case '4':
                set_channel();
                break;
            case 'A':
                break;
            default:
                choice = 0;
                break;
        }
    }
} void set_channel(void)
{
    char choice;
    int errr;

choice = 0;
    write_lcd(0x01, 0);
    row1();
    printf("1. Analog output 1");
    row2();
    printf("2. Analog output 2");
    while (!choice) {
        write_lcd(0x0e, 0);
        write_lcd(0xe7, 0);
        choice = _getkey();
        switch(choice) {
            case '1':
                set_var((unsigned int) 0);
                break;
            case '2':
                set_var((unsigned int) 1);
                break;
            case 'A':
                break;
            default:
                choice = 0;
                break;
        }
    }
}
```

```c
void set_var(unsigned int channel)
{
    char choice;
    int errr;

choice = 0;
    write_lcd(0x01, 0);
    row1();
    printf("1. Crosslink Temp.");
    row2();
    printf("2. Crosslink Time");
    row3();
    printf("3. Temperature");
    while (!choice) {
        row4();
        printf("4. Torque");
        write_lcd(0x0e, 0);
        write_lcd(0xe7, 0);
        choice = _getkey();
        switch(choice) {
            case '1':
                aindex[channel] = 0;
                break;
            case '2':
                aindex[channel] = 1;
                break;
            case '3':
                aindex[channel] = 2;
                break;
            case '4':
                aindex[channel] = 3;
                break;
            case 'A':
                break;
            default:
                choice = 0;
                break;
        }
        if (channel)
            write_eeprom((char *) &aindex[1], a1_back, 1);
        else
            write_eeprom((char *) &aindex[0], a0_back, 1);
    }
} void set_outputs()
{
    xdata char c;

do {
        item("1. Outputs low", "2. Outputs High", "");
        c = _getkey();
        if (c == '1') {
            manualao = one;
            PWM0 = (unsigned char) 0xff;
            PWM1 = (unsigned char) 0xff;
        }
        else if (c == '2') {
            manualao = one;
            PWM0 = 0;
            PWM1 = 0;
        }
        else if (c == '3') {
            manualao = 0;
        }
    } while (c == '1' || c == '2' || c == '3');
} void cal_temp(void)
{
    char choice;
```

```c
        int errr;

choice = 0;
    write_lcd(0x01, 0);
    row1();
    printf("1. Set offset");
    row2();
    printf("2. Set span");
    row3();
    printf("3. View Calibration");
    while (!choice) {
        write_lcd(0x0c, 0);
        write_lcd(0xe7, 0);
        choice = _getkey();
        switch(choice) {
            case '1':
                item( "Enter the temper-", "ature of the fluid",
                        "in Farenheit");
                do {
                    lastline();
                    getinput();
                    } while ((errr = sscanf(keybuffer, "%f", &ztemp)) ==
                            EOF || errr == 0);
                zadc = temperature;
                write_eeprom((char *) &ztemp, zt_back, 4);
                write_eeprom((char *) &zadc, za_back, 2);
                find_toffset();
                find_temp_val();
                break;
            case '2':
                item( "Enter the temper-", "ature of the fluid",
                        "in Farenheit");
                do {
                    lastline();
                    getinput();
                    } while ((errr = sscanf(keybuffer, "%f", &stemp)) ==
                            0 || errr == EOF);
                sadc = temperature;
                find_tslope();
                find_toffset();
                find_temp_val();

break;
            case '3':
                write_lcd(0x01, 0);
                row1();
                printf("%5.1f", ztemp);
                row2();
                printf("%4u", zadc);
                row3();
                printf("%5.1f", toffset);
                row4();
                printf("%-8.6f", tslope);
                _getkey();
                break;
            case 'A':
                break;
            default:
                choice = 0;
                break;
        }
        setup_temp_outputs();
        }
} void item(char *cptr1, char *cptr2, char *cptr3)
{
    write_lcd(0x01, 0);
    row1();
    printf(cptr1);
    row2();
    printf(cptr2);
    row3();
    printf(cptr3);
```

```c
} void find_torq_val(void)
{
    float tt1;
    int errr;

item("Enter the torque", "at 20 mA.", "");
    do {
        lastline();
        getinput();
        } while( (errr = sscanf(keybuffer, "%f", &tt1)) == 0 ||
            errr == EOF);
    tt1 = tt1 * 2046.0 / TORQUEC / GEAR;
    storq_ao = (int) (-255.0 * 2048.0 / tt1);
    otorq_ao = (int) (-(-255.0 / tt1) * (tt1 + (nlc * 2046.0)));
    write_eeprom((char *) &storq_ao, storq_back, 2);
    write_eeprom((char *) &otorq_ao, otorq_back, 2);
} void find_temp_val(void)
{
    xdata float tt1, tt2, tt3;

tt1 = (32.0 - toffset) / tslope;
    tt2 = (212.0 - toffset) / tslope;
    tt3 = -255.0 / (tt2 - tt1);
    stemp_ao = (long)(tt3 * 32768.0);
    otemp_ao = (int)(-(tt3 * tt2));
} void enter_max_heat_rate(void)
{
    xdata int errr;
    xdata char response, sc_ptr, gw_ptr, entry_ptr;
    xdata unsigned char ctemp;
    xdata float ftemp, ftemp2;

write_lcd(0x01, 0);
    row1();
    printf("Mhrt = %5.2f%cF/min.", max_hrate, DEG);
    row2();
    printf("1. Enter value");
    row3();
    printf("2. Use table");
    write_lcd(0xe7, 0);
    response = _getkey();
    if (response == '1') {
        write_lcd(0x01, 0);
        row1();
        printf("Enter the maximum");
        row2();
        printf("heat rate of the");
        row3();
        printf("heater (%cF/min):", DEG);
        do {
            lastline();
            getinput();
            } while ((errr = sscanf(keybuffer, "%f", &max_hrate))
                == 0 || errr == EOF);
    }
    else if (response == '2') {
        write_lcd(0x01, 0);
        row1();
        printf("1. %s", lut_ptr[0].label);
        row2();
        printf("2. %s", lut_ptr[1].label);
        row3();
        printf("3. %s", lut_ptr[2].label);
        row4();
        printf("4.  <NEXT WINDOW>");
        write_lcd(0xe7, 0);
```

```c
                    response = _getkey();
                    if (response < '1' || response > '3') {
                        write_lcd(0x01, 0);
                        row1();
                        printf("1. %s", lut_ptr[3].label);
                        row2();
                        printf("2. %s", lut_ptr[4].label);
                        row3();
                        printf("3. %s", lut_ptr[5].label);
                        row4();
                        printf("4.  QUIT");
                        write_lcd(0xe7, 0);
                        response = _getkey();
                        if (response >= '1' && response <= '3')
                            entry_ptr = (response - '1') + 3;
                        else
                            entry_ptr = 15;
                    }
                    else
                        entry_ptr = (response - '1');
                    if (entry_ptr < 6) {
                        do {
                            write_lcd(0x01, 0);
                            row1();
                            printf("%s", lut_ptr[entry_ptr].label);
                            row2();
                            printf("Enter sand concen-");
                            row3();
                            printf("tration (lb./gal.):");
                            write_lcd(0xe0, 0);
                            getinput();
                        } while (keybuffer[0] != '\0' && ((errr = sscanf(keybuffer, "%f",
                                &ftemp)) == 0 || errr == EOF || ftemp < 0.0 || ftemp > 32.0));
                        if (keybuffer[0] != '\0') {
                            do {
                                write_lcd(0x01, 0);
                                row1();
                                printf("%s", lut_ptr[entry_ptr].label);
                                row2();
                                printf("Enter gel weight");
                                row3();
                                printf("(lb.):");
                                write_lcd(0xe0, 0);
                                getinput();
                            } while (keybuffer[0] != '\0' && ((errr = sscanf(keybuffer, "%bu",
                                    &ctemp)) == 0 || errr == EOF || ctemp < 10 || ctemp > 200));
                            if (keybuffer[0] != '\0') {
                                if (ctemp < lut_ptr[entry_ptr].gelw[0])
                                    max_hrate = find_mhrt(entry_ptr, 0, ftemp);
                                else if (ctemp > lut_ptr[entry_ptr].gelw[1])
                                    max_hrate = find_mhrt(entry_ptr, 1, ftemp);
                                else
                                    ftemp2 = find_mhrt(entry_ptr, 0, ftemp);
                                    ftemp = find_mhrt(entry_ptr, 1, ftemp);
                                    max_hrate = ((float)(ctemp - lut_ptr[entry_ptr].gelw[0]) /
                                            (float)(lut_ptr[entry_ptr].gelw[1] -
                                            lut_ptr[entry_ptr].gelw[0])) * (ftemp - ftemp2) +
                                            ftemp2;
                            }
                        }
                    }
        write_eeprom((char *) &max_hrate, hrate_back, 4);
    } void enter_heat_rate(void)
{
    int errr;

write_lcd(0x01, 0);
    row1();
    printf("Enter the ramp");
    row2();
    printf("rate for the ");
```

```c
        row3();
        printf("sample (%cF/min):", DEG);
        do {
            lastline();
            getinput();
        } while ((errr = sscanf(keybuffer, "%f", &rate)) == 0 || errr ==
                EOF || rate < .01 || rate > 40.0);
        write_eeprom((char *) &rate, rate_back, 4);
    } void enter_max_temp(void)
    {
    int errr;

write_lcd(0x01, 0);
    row1();
    printf("Enter the temper-");
    row2();
    printf("ature to turn off");
    row3();
    printf("heater (%cF):", DEG);
    do {
        lastline();
        getinput();
    } while ((errr = sscanf(keybuffer, "%f", &maxtemp)) == 0 || errr ==
            EOF || maxtemp < 32.0 || maxtemp > 200.0);
    compadc = (unsigned int) (maxtemp - toffset) / tslope;
    write_eeprom((char *) &maxtemp, mtemp_back, 4);
    }

/*
        find_toffset() calculates the offset value of the temperature
        probe's calibration.
        zadc is adc counts s^2, ztemp is deg F, toffset is deg F.
    */ void find_toffset(void)
    {
    toffset = ztemp - tslope * (float) zadc;
    write_eeprom((char *) &toffset, toff_back, 4);
    }

/*
        find_tslope() calculates the slope value of the temperature
        probe's calibration.
        tslope is deg F / (adc counts s^2).
    */ void find_tslope(void)
    {
    tslope = (stemp - ztemp) / ((float) ((int) sadc - (int) zadc));
    write_eeprom((char *) &tslope, tsl_back, 4);
    }

/*
        start_heat()  initializes heat variables to start heater
        control.
    */ void start_heat(void)
    {
    manualht = 0;
    tsetpt = ((unsigned long) temperature) << 7;
    pulse2 = 0;
    count5sec = 0;
    feedforward2 = (100 * rate) / max_hrate;
    deltatemp = 0;
    if (rate >= 5.0)
        deltatemp = (unsigned char) ((2.5 * rate)/ ((max_hrate - 5.0) *
```

```
                              tslope));
        heatpulse = feedforward2 * ffwdm;
        if (heatpulse > 100)
                heatpulse = 100;
        v2 = heatpulse;
        if (feedforward2 > 100)
                feedforward2 = 100;
        if (feedforward2 < 0)
                feedforward2 = 100;
        controlflag = 0;
        rampflag = 0;
        ratesp = (int)((rate * 21.33333) / tslope);
                /* 21.33333 is 128 / 1min per 6 10sec. */
        deltarate = (unsigned int) (.15 * (float) ratesp);
        xlinksflag = 0;
        xlinkeflag = 0;
        pointflag = 0;
        tempptr = tempsave;
        const_temp = 0;
        mslope = mslp;
        xthresh = 15360;
        sumx = 0;
        sumy = 0;
        sumxy = 0.0;
        sumx_2 = 0.0;
        slopeflag = 0;
        placeptr = 0;
        index = 0;
        }

/*                      item("1. EPROM", "2. X-RAM","3. E2PROM");
                response = _getkey();
                if (response == '1')
                        tptr = (char *) 0x50000L;
                else if (response == '2')
                        tptr = (char *) 0x20800L;
                else
                        tptr = (char *) 0x24000L;
                item("Enter address", "offset in dec:","");
                do{
                        lastline();
                        getinput();
                        } while((errr = sscanf(keybuffer, "%u", &poff) == 0)
                                || errr == EOF);
                item("1. 16 char string", "2. uchar", "3. float");
                tptr = tptr + poff;
                choice = _getkey();
                write_lcd(0x01, 0);
                row1();
                if (choice == '1') {
                        printf("%s", tptr);
                        }
                else if (choice == '2') {
                        printf("%bu", *(unsigned char *)tptr);
                        }
                else {
                        printf("%7.3f", *(float *)tptr);
                        }
                _getkey();
                break;

*/ void init(void)
        {
        for (loop = 0; loop < 10; loop++)
                ones[loop] = 0;
        loop = 0;
        /* set lcd enable low */
        RT2 = 0;
        /*****************************************************************
            Initialize & Start Timer 1 as Serial Port Baud Rate Generator
```

The following equation is used to determine the proper setting for
the timer 1 high.

$$\text{Baud Rate} = \frac{2^{SMOD}}{32} \times \frac{\text{Oscillator Frequency}}{12 \times [256 - (TH1)]}$$

$$TH1 = 256 - \frac{K \times \text{Oscillator Frequency}}{384 \times \text{Baud Rate}} \quad ; \quad K = 2^{SMOD}$$

$$TH1 = 247 \quad (SMOD = 1 \ \& \ \text{Baud Rate} = 9600)$$

```
    TMOD is set for:
        TMOD.7 - Timer enabled by TR1 control bit (in TCON)
        TMOD.6 - Timer operation
        TMOD.5 - > 8-bit Auto-Reload Timer/Counter
        TMOD.4 - /
    TCON is set for:
        TCON.6 - Start timer
    PCON is set for:
        PCON.7 - Double baud rate
***************************************************************/
  PCON |= 0x80;
  TMOD |= 0x25; /* Timer 0 in 16bit counter mode, sw control */
  TH1 = (unsigned char) 0xf7;
  TR1 = one;

/**************************************************************
   Initialize Serial Port
        SCON is set for:
            SCON.7 - > 8-bit UART with variable baud rate
            SCON.6 - /
            SCON.5 - Single porcessor environment
            SCON.4 - Disable receiver
***************************************************************/
  S0CON = (unsigned char) 0x50;
  S0BUF = (unsigned char) 'M';
  PS0 = one; /* high priority */
  ES0 = one;
  /* set up timer 0 for a frequency input */
  ET0 = one;
  PT0 = one;
  TR0 = one;
  /* turn off motor fets */
  /* set up timer 2 for .02 sec interrupt */
  ECM0 = one;
  PCM0 = 0;    /* low priority */
  t2comp0 = (unsigned int) 26666;
  CMH0 = ((unsigned char)(t2comp0 >> 8));
  CML0 = ((unsigned char) (t2comp0 & 0x00ff));
  TM2CON = (unsigned char) 0X01;
  /* set up Heater pwm*/
  pulse2 = 0;
  pwmcount = 0;
  manualht = one;
  /* turn off heater */
  T1 = 0;
  /* make sure output is high for frequency input */
  T0 = one;
  /* set pwm pulse width to maximum frequency */
  PWM2 = (unsigned char) 0x00;
  /* set pwm1 to off */
  PWM0 = (unsigned char) 0xff;
  adac = 0;
  dacout();
  manualmo = one;
  /* set analog out to zero */
  PWM1 = (unsigned char) 0xff;
  /* set up ADC to read channel 0 only */
  PAD = one;   /* high priority */
  EAD = one;
  CT0I = one;
  CT1I = one;
```

```
            CT2I = one;
            CT3I = one;
            /* enable interrupts */
            keypress = 0;
            kflag = 0;
            kcountu = 0;
            kcountd = 0;
            skiptime = 1;
            rbit = 0;
            newkey = 0x20;
            lcd_notserial = one;
            xtime = 0;
            xtemp = 0;
            const_temp = 0;
            calcflag = 0;
            manualao = 0;
            manmoop = 0;
            motorout = 0;
            aindex[0] = 0;
            aindex[1] = 0;
            EA = one;
            } void cal_init(void)
            {
            xdata long *chk;
            read_eeprom((char *) &ib1, ib1_back, 2);
            if (ib1 > 2000 || ib1 < 0)
                    ib1 = 2;
            read_eeprom((char *) &pb1, pb1_back, 2);
            if (pb1 > 2000 || pb1 < 0)
                    pb1 = 15;
            read_eeprom((char *) &ib2, ib2_back, 2);
            if (ib2 > 100 || ib2 < 0)
                    ib2 = 2;
            read_eeprom((char *) &pb2, pb2_back, 2);
            if (pb2 > 20000 || pb2 < 0)
                    pb2 = 200;
            read_eeprom((char *) &ib3, ib3_back, 2);
            if (ib3 > 30 || ib3 < 0)
                    ib3 = 1;
            read_eeprom((char *) &pb3, pb3_back, 2);
            if (pb3 > 100 || pb3 < 0)
                    pb3 = 3;
            read_eeprom((char *) &rpm_setpt, rpm_back, 2);
            if (rpm_setpt > 300 || rpm_setpt < 1)
                    rpm_setpt = 150;
            read_eeprom((char *) &nlc, nlc_back, 4);
            chk = (long *)&nlc;
            if (nlc <= 0.0 || nlc > 0.5 || *chk == 0xffffffffL)
                    nlc = 0.25;
            read_eeprom((char *) &rate, rate_back, 4);
            if (rate < .01 || rate > 32.0)
                    rate = 14.5;
            read_eeprom((char *) &max_hrate, hrate_back, 4);
            if (max_hrate < 0 || max_hrate > 50.0)
                    max_hrate = 39.0;
            setpoint1 = (int) (rpm_setpt/ RPM_CONST);
            error_rpm = (int) (.9 * setpoint1);
            read_eeprom((char *) &toffset, toff_back, 4);
            chk = (long *) &toffset;
            if (toffset < 15 || toffset > 35 || *chk == 0xffffffffL)
                    toffset = 22;
            read_eeprom((char *) &tslope, tsl_back, 4);
            chk = (long *) &tslope;
            if (tslope < 0.02 || tslope > 0.07 || *chk == 0xffffffffL)
                    tslope = 0.0488598;
            read_eeprom((char *) &ztemp, zt_back, 4);
            chk = (long *) &ztemp;
            if (ztemp < 0.0 || ztemp > 230.0 || *chk == 0xffffffffL) {
                    ztemp = 32.0;
                    zadc = 3992;
                    }
            read_eeprom((char *) &zadc, za_back, 2);
```

```
if (zadc < 0 || zadc > 4092) {
    zadc = 3992;
    ztemp = 32.0;
}
read_eeprom((char *) &maxtemp, mtemp_back, 4);
chk = (long *) &maxtemp;
if (maxtemp < 32.0 || maxtemp > 210.0 || *chk == 0xffffffffL)
    maxtemp = 150.0;
compadc = (unsigned int) (maxtemp - toffset) / tslope;
read_eeprom((char *) &storq_ao, storq_back, 1);
if (storq_ao < 500 || storq_ao > 2500)
    storq_ao = 1366;
read_eeprom((char *) &otorq_ao, otorq_back, 1);
if (otorq_ao < 50 || otorq_ao > 1000)
    otorq_ao = 543;
find_temp_val();
read_eeprom((char *) &scounts, sc_back, 1);
if (scounts < 5 || scounts > 50)
    scounts = 14;
read_eeprom((char *) &mslp, mslp_back, 4);
chk = (long *) &mslp;
if (mslp < 0.001 || mslp > 0.05 || *chk == 0xffffffffL)
    maxtemp = 0.004;
read_eeprom((char *) &ffwdm, ffwdm_back, 4);
chk = (long *) &ffwdm;
if (ffwdm < 1.0 || ffwdm > 2.0 || *chk == 0xffffffffL)
    ffwdm = 1.5;
read_eeprom((char *) &bht, bht_back, 4);
chk = (long *) &bht;
if (bht < 32.0 || bht > 400.0 || *chk == 0xffffffffL)
    bht = 200.0;
read_eeprom((char *) &start_temp, stt_back, 4);
chk = (long *) &start_temp;
if (start_temp < 32.0 || start_temp > 400.0 || *chk == 0xffffffffL ||
        start_temp >= bht) {
    start_temp = 70.0;
    bht = 200.0;
}
read_eeprom((char *) &vtp, vtp_back, 4);
chk = (long *) &vtp;
if (vtp < 10.0 || vtp > 999999 || *chk == 0xffffffffL)
    vtp = 4000;
read_eeprom((char *) &dhrate, bpm_back, 4);
chk = (long *) &dhrate;
if (dhrate < 0.1 || dhrate > 200.0 || *chk == 0xffffffffL)
    dhrate = 20.0;
read_eeprom((char *) &aindex[0], a0_back, 1);
if (aindex[0] > 3)
    aindex[0] = 1;
read_eeprom((char *) &aindex[1], a1_back, 1);
if (aindex[1] > 3)
    aindex[1] = 0;
setup_torq_outputs();
setup_temp_outputs();
}
```

```
/*
    Timer 0 interrupt (every .02 seconds)
*/ include <stdio.h>
include "reg552.h"
#include "xdef.h"
define one (bit) 1 extern void read_keypad(char *);
extern void decode_key(void);
unsigned int xtemp_output(void);
unsigned int xtime_output(void);
unsigned int temp_output(void);
unsigned int torq_output(void);
void dacout(void);
void dacout_a1(unsigned int adac1);
void dacout_a2(unsigned int adac2);

extern xdata char newkey;
extern xdata unsigned int adac, compadc, motorout, loopcheck, loopcheck1[],
        temp2outoff, temp2outrng, torq2outrng, torq2outoff;
extern idata bit manmoop, manualao;
extern xdata float xtime, xtemp;
extern xdata unsigned char aindex[2];

idata unsigned int t2comp0, pb1, ib1, setpoint1, pb2, ib2,
        pb3, ib3, arate, adc[5], ratesp, freq;
idata unsigned char feedforward2, count5sec, pwmcount, ind, deltatemp;
idata unsigned long time, tsetpt;
idata long i1, v1, i2;
idata bit manualmo, hibit, lobit, manualht, controlflag, rampflag,
        send, in_flag, xlinksflag, xlinkeflag, endtemp,
        const_temp, calcflag, pointflag;
idata char loop, loop2;
idata int v2;
xdata char ascii_in;
xdata unsigned char rcount0, rcount1, rcount2, rcount3, rcount4, rcount5,
        rcount6, bindex, orpmcount, index, daskip, skiptime, pulse2;
xdata unsigned int ones[10], buffer[11], temperature, deltarate, *tempptr,
        xthresh, torquehold, mxthresh;
xdata long tofft, offset_time, stemp_ao, timehold, timeh1;
xdata int error_rpm, storq_ao, otorq_ao, otemp_ao;

void t2compare0(void) interrupt 11
    {
    idata int error2, error1, error3;
    idata unsigned int dout;

P4 = (P4 & 0xfd);
    time += 2L;
    if (hibit) {
        /* interrupt every .02 sec */
        t2comp0 += (unsigned int) 26667;
        hibit = 0;
        lobit = 0;
        }
    else {
        t2comp0 += (unsigned int) 26666;
        if (lobit)
            hibit = one;
        else
            lobit = one;
        }
    CMH0 = ((unsigned char) (t2comp0 >> 8));
    CML0 = t2comp0 & 0x00ff;
    if (loopcheck1[loop] < loopcheck)
        loopcheck1[loop] = loopcheck;
    loopcheck = 0;
    pwmcount++;
    if (pwmcount > 100) {
        pwmcount = 0;
```

```
            if (pulse2)
                T1 = one;
        }
    if (pwmcount > pulse2)
        T1 = 0;
    switch (loop) {
        case 0:
            if (adc[4] > 1022) {
                manualmo = one;
                pulse2 = 0;
                manualht = one;
                P4 |= 0x04;
            }
            if (rampflag && !loop2) {
                if (!xlinksflag) {
                    offset_time = (time - 2L);
                    xlinksflag = one;
                    xlinkeflag = 0;
                    endtemp = 0;
                    daskip = 0;
                    index = 0;
                    pointflag = 0;
                }
                if (adc[4] > 950) {
                    xlinkeflag = one;
                    calcflag = one;
                }
                if (!xlinkeflag) {
                    if (!endtemp) {
                        *tempptr = temperature;
                        tempptr-+;
                        if (tempptr > 0x20ff3)
                            endtemp = one;
                    }
                    daskip++;
                    if (daskip > skiptime) {
                        torquehold = adc[4];
                        timeh1 = timehold;
                        timehold = time - offset_time - 2L;
                        pointflag = one;
                        daskip = 0;
                    }
                    else {
                        pointflag = 0;
                    }
                }
            }
            switch(aindex[0]) {
                case 0:
                    dout = xtemp_output();
                    break;
                case 1:
                    dout = xtime_output();
                    break;
                case 2:
                    dout = temp_output();
                    break;
                case 3:
                    dout = torq_output();
                    break;
                default:
                    dout = xtemp_output();
                    break;
            }
            dacout_a1(dout);
            break;
        case 1:
            TR0 = 0;
            freq = TH0;
            freq = freq << 8;
            freq |= TL0;
            TL0 = 0;
            TH0 = 0;
            TR0 = one;
            ind++;
```

```
        if (ind > 9)
            ind = 0;
    ones[ind] = freq;
    freq = ones[0] + ones[1] + ones[2] + ones[3] + ones[4] +
            ones[5] + ones[6] + ones[7] + ones[8] - ones[9];
    if (!loop2) {
        rcount0 = rcount1;
        rcount1 = rcount2;
        rcount2 = rcount3;
        rcount3 = rcount4;
        rcount4 = rcount5;
        rcount5 = rcount6;
        count5sec++;
            /* count5sec is used every 15 second */
        if (count5sec == 15)
            count5sec = 0;
    }
    loop2++;
        /* loop2 is used every 1 seconds */
    if (loop2 > 9)
        loop2 = 0;
    if (loop2 == 0)
    if (i2 < 0)
        i2 = 0;
    else if (i2 > 104857600L)
        i2 = 104857600L;
    switch(aindex[1]) {
        case 0:
            dout = xtemp_output();
            break;
        case 1:
            dout = xtime_output();
            break;
        case 2:
            dout = temp_output();
            break;
        case 3:
            dout = torq_output();
            break;
        default:
            dout = xtime_output();
            break;
    }
    dacout_a2(dout);
    break;
case 2:
    if (freq < error_rpm) {
        if (orpmcount > 10 && !manualmo) {
            manualmo = one;
            pulse2 = 0;
            manualht = one;
            P4 |= 0x04;
        }
    }
    else {
        orpmcount++;
        if (orpmcount > 11)
            orpmcount = 11;
    }
    error1 = setpoint1 - freq;
    v1 = (((((long)error1 * (long) pb1) << 5) + i1) >> 10);
    i1 += ((long)error1 * (long)ib1 * (long)pb1);
    if (v1 > 4095)
        v1 = 4095;
    if (v1 < 0)
        v1 = 0;
    if (!manualmo) {
        adac = (unsigned int) v1;
        dacout();
    }
    if (manmoop) {
        adac = motorout;
        dacout();
    }
    if (i1 > 4193280L)
```

```
                i1 = 4193280L;
            if (i1 < 0)
                i1 = 0;
        break;
    case 3:
        if (!loop2) {
            temperature = adc[0] + adc[1] + adc[2] + adc[3];
            buffer[bindex] = temperature;
            if (bindex == 10) {
                if (buffer[10] < buffer[0])
                    rcount6 = 0;
                else
                    rcount6 = (unsigned char) (buffer[10] -
                            buffer[0]);
                bindex = 0;
            }
            else {
                if (buffer[bindex] < buffer[bindex+ 1])
                    rcount6 = 0;
                else
                    rcount6 = (unsigned char) (buffer[bindex] -
                            buffer[bindex + 1]);
                bindex++;
            }
            arate = ((unsigned int) rcount0 * 4 +
                    (unsigned int) rcount1 * 50 +
                    (unsigned int) rcount2 * 122 +
                    (unsigned int) rcount3 * 160 +
                    (unsigned int) rcount4 * 122 +
                    (unsigned int) rcount5 * 50 +
                    (unsigned int) rcount6 * 4) >> 2;
            /* fir kaiser filter .025 ripple, .01 fp, .3
                    fs, 1 fsa * 2^9 */
        }
        break;
    case 4:
        if (!loop2) {
            if (!manualht) {
                if (temperature > (compadc - 204)) {
                    /* 204 is approx. 10 deg F */
                    if (!const_temp) {
                        const_temp = one;
                        pulse2 = 0;
                        v2 = 0;
                        i2 = 0;
                    }
                    if ((tsetpt >> 7) > compadc)
                        tsetpt = compadc << 7;
                }
                if (!rampflag) {
                    if (((int) temperature) - ((int)  (tsetpt >> 7))
                            > deltatemp) {
                        rampflag = one;
                    }
                }
                if (!controlflag) {
                    if (((int) arate) >= ((int) ratesp - (int)
                            deltarate)) {
                        rampflag = one;
                        controlflag = one;
                        count5sec = 0;  /* was 14 */
                         if (((int) (tsetpt >> 7)) - ((int)
                                temperature) < deltatemp)
                                v2 = (int) feedforward2;
                        i2 = ((long) v2 << 20);
                    }
                }
                if (rampflag) {
                    tsetpt += (ratesp / 10);
                    if (tsetpt > (long) compadc << 7)
                        tsetpt = (long) compadc << 7;
                }
                if (count5sec == 14 && controlflag) {
                    error2 = (int)((long) tsetpt >> 7) -
                            (int) temperature;
```

```c
                                error3 = (int) ratesp - (int) arate;
                                if (const_temp)
                                    error3 = 0;
                                v2 = ((((long)error2 * (long) pb2) << 10)
                                        + (((long)error3 * (long) pb3) << 10)
                                        + i2) >> 20);
                                i2 += (((long)error2 * (long)ib2 * (long)pb2)
                                        + ((long)error3 * (long)ib3 *
                                            (long) pb3));
                                if (v2 > 100)
                                    v2 = 100;
                                else if (v2 < 0)
                                    v2 = 0;
                                }
                            pulse2 = (unsigned char) v2;
                            }
                    }
                break;
            default:
                break;
            }
    loop++;
    if (loop > 4)
        loop = 0;
    ADCON |= 0x08;
    read_keypad(&newkey);
    decode_key();
    P4 = (P4 | 0x02);
    TM2IR &= 0xef;
    } void adcread(void) interrupt 10
    {
    unsigned int adc0;

adc0 = ADCH;
    adc0 = adc0 << 2;
    adc0 |= ((ADCON & 0xc0) >> 6);
    adc[loop] = adc0;
    ADCON &= 0x00;
    if (loop == 3)
        ADCON |= 0x01;
    else ADCON &= 0x00;
    } void serial0 (void) interrupt 4
    {
    if (TI)
        send = 0;
    else if (RI) {
        ascii_in = S0BUF;
        in_flag = one;
        }
    TI = 0;
    RI = 0;
    } unsigned int xtime_output()
    {
    unsigned int temp1;

temp1 = (unsigned int) ((long) (xtime * 100.0) * 3044L / 72000L + 761);
    if (temp1 > 4095)
        temp1 = 4095;
    return (temp1);
    } unsigned int xtemp_output()
    {
    unsigned int temp1;
```

```c
    if (xtemp < 32.0)
        temp1 = 0;
    else temp1 = (unsigned int) (xtemp * 16.0 - 512.0);
    temp1 = (unsigned int) ((long) temp1 * 3044L / 2660L - 761);
    if (temp1 > 4095)
        temp1 = 4095;
    return (temp1);
    } unsigned int temp_output()
    {
    unsigned int temp1;

if (temperature < temp2outoff)
        temp1 = 0;
    else temp1 = (temperature - temp2outoff);
    temp1 = (unsigned int) ((long) temp1 * 3044L / temp2outrng + 761);
    if (temp1 > 4095)
        temp1 = 4095;
    return (temp1);
    } unsigned int torq_output()
    {
    unsigned int temp1;

if (adc[4] < torq2outoff)
        temp1 = 0;
    else temp1 = (adc[4] - torq2outoff);
    temp1 = (unsigned int) ((long) temp1 * 3044L / (long) torq2outrng + 761);
    if (temp1 > 4095)
        temp1 = 4095;
    return (temp1);
    } void dacout()
    {
    *(char *) 0x22000L = (char) (adac & 0x0f);
    *(char *) 0x22001L = (char) ((adac >> 4) & 0x0f);
    *(char *) 0x22002L = (char) ((adac >> 8) & 0x0f);
    *(char *) 0x22003L = (char) (0x01);

/*
    *(char *) 0x2c000L = (char) (adac & 0x0f);
    *(char *) 0x2c001L = (char) ((adac >> 4) & 0x0f);
    *(char *) 0x2c002L = (char) ((adac >> 8) & 0x0f);
    *(char *) 0x2c003L = (char) (0x01);
    */
    } void dacout_a1(unsigned int a1dac)
    {
    if (!manualao)
        PWM0 = ((unsigned char) 255 - (unsigned char) (a1dac >> 4));
    /*
    *(char *) 0x2a000L = (char) (a1dac & 0x0f);
    *(char *) 0x2a001L = (char) ((a1dac >> 4) & 0x0f);
    *(char *) 0x2a002L = (char) ((a1dac >> 8) & 0x0f);
    *(char *) 0x2a003L = (char) (0x01);
    */
    } void dacout_a2(unsigned int a2dac)
    {
    if (!manualao)
        PWM1 = ((unsigned char) 255 - (unsigned char) (a2dac >> 4));
    /*
    *(char *) 0x2e000L = (char) (a2dac & 0x0f);
    *(char *) 0x2e001L = (char) ((a2dac >> 4) & 0x0f);
    *(char *) 0x2e002L = (char) ((a2dac >> 8) & 0x0f);
    *(char *) 0x2e003L = (char) (0x01); */
```

```c
/*
    serial port routines and display routines.
*/ include <stdio.h>
include "reg552.h"
#include "lcdef.h"
#include "xdef.h"

define one (bit) 1
#define LCD *((char *) 0x28000L)

/*#define XON  0x11
define XOFF 0x13 */ extern idata unsigned long time, tsetpt;
extern idata unsigned int adc[], freq;
extern idata bit lcd_notserial, send, xlinkeflag, calcflag, pointflag,
        slopeflag;
extern idata long v1;
extern xdata unsigned int adac, temperature, xthresh, torquehold;
extern xdata unsigned long time_s;
extern xdata float speed, faren, torque, tempsp, tslope, toffset, nlc;
extern xdata long offset_time, timehold;
extern xdata unsigned char pwmm0, pwmm1, index, placeptr, pulse2;

xdata float xslope, xoffset, xdiv, mslope, sumx_2, sumxy, xtemp, xtime;
xdata unsigned int torques[15];
xdata long   times[15], sumx, sumy;
xdata unsigned char nocounts, scounts;
extern xdata char *addr_ptr, *value_ptr;

void write_lcd(char info, bit rs);
bit lcd_busy(void);
void send_ascii_out(void);
void write_eeprom(char *value, char *addr, int bytes);

int putchar(char c)
    {
    if (lcd_notserial) {
        /* this function assumes a blank line on the lcd display or a
            string formated to 20 characters */
        write_lcd(c, 1);
        return((int) c);
        }
    else {
        if (c == '\n')  {
            while (send);
            send = one;
            S0BUF = (char) 0x0d;
            }
        while (send);
        send = one;
        return ((int) (S0BUF = c));
        }
    } void serial_data(void)
    {
    float tempf1, tempf2;
    if ( !(time <= time_s)) {
        time_s = time + 98L;
        if (!xlinkeflag) {
            if (pointflag) {
                pointflag = 0;
                sumx += timehold;
                sumx_2 += (float) ((float) timehold *
                        (float) timehold);
                sumxy += (float) ((long) torquehold *
                        timehold);
```

```
            sumy += torquehold;
            if (index == 15) {
                sumx -= times[placeptr];
                sumx_2 -= (float) ((float) times[placeptr] *
                            (float) times[placeptr]);
                sumxy -= (float) ((long) torques[placeptr] *
                            times[placeptr]);
                sumy -= torques[placeptr];
                times[placeptr] = timehold;
                torques[placeptr] = torquehold;
                if (xthresh == 15360)
                    xthresh = sumy;
                else if (sumy < xthresh)
                    xthresh = sumy;
                xdiv = ((float) index * sumx_2 - (float) sumx * (float) sumx);
                if (xdiv) {
                    xslope = (float) ((float) index * sumxy - (float) sumx *
                                    (float) sumy) / xdiv;
                    }
                else {
                    xslope = 0;
                    }
                if (xslope >= mslope) {
                    mslope = xslope;
                    xoffset = (float) ((float)sumy * (float)sumx_2 -
                                (float) sumx * sumxy) / xdiv;
                    nocounts = 0;
                    slopeflag = one;
                    }
                else if (slopeflag) {
                    nocounts++;
                    if (nocounts > scounts) {
                        xlinkflag = one;
                        calcflag = one;
                        }
                    }
                placeptr++;
                if (placeptr > 14) {
                    placeptr = 0;
                    }
                }
            else {
                times[index] = timehold;
                torques[index] = torquehold;
                index++;
                }
            }
        }
    if (calcflag) {
        if (!slopeflag) {
            xdiv = ((float) index * sumx_2 - (float) sumx *
                    (float) sumx);
            mslope = (float) ((float) index * sumxy - (float) sumx *
                    (float) sumy) / xdiv;
            xoffset = (float) ((float)sumy * (float)sumx_2 -
                    (float) sumx * sumxy) / xdiv;
            }
        if (mslope > 0) {
            xthresh = xthresh / 15;
            xtime = (((float) xthresh - xoffset) / mslope) / 100.0;
            if (xtime < 0) {
                xtime = 0;
                xtemp = (float) (*(unsigned int *) (tempsave));
                }
            else {
                tempf1 = xtime - (float) ((int) xtime);
                tempf2 = (float) (*(unsigned int *) (tempsave + (unsigned int)
                        xtime + 1)) - (float) (*(unsigned int *) (tempsave +
                        (unsigned int) xtime));
                xtemp = (float) (*(unsigned int *) (tempsave +
                        (unsigned int) xtime)) - tempf2 * tempf1;
                }
            xtemp = xtemp * tslope + toffset;
            if (xtemp < 32.0)
                xtemp = 32.0;
```

```
                    if (xtemp > 212.0)
                        xtemp = 212.0;
                    }
                calcflag = 0;
                }
            faren = ((float) temperature) * tslope + toffset;
            tempsp = ((((float) tsetpt) / 128.0) * tslope + toffset);
            speed = freq * RPM_CONST;
            torque = ((((float) adc[4]) * TORQUE_COUNTS) - nlc) * TORQUE_GEAR;
                /* .000977517 is 1 amp /1023 counts   was below */
                /* .00048876 is .5 amps/1 ohm / 1023 counts per volt */
            if (torque < 0)
                torque = 0;
            lcd_notserial = 0;
            printf("%8.1f %5.1f", ((float) (time - offset_time) / 100.0),
                    faren);
            printf(" %5.1f %3bu", tempsp, pulse2);
            printf(" %5.2f %4u %5.1f", torque, adac[4], speed);
            printf(" %5.1f %5.1f\n", xtime , xtemp);
            lcd_notserial = one;
            }
        }

/* write and read EEPROM */ void write_eeprom(char *value, char *addr, int bytes)
    {
    xdata int i;
    xdata unsigned long timeout;

for (i = 0; i < bytes; i++) {
        addr[i] = value[i];
        timeout = time + 3;
        while (addr[i] != value[i] && timeout > time);
        }
    } void read_eeprom(char *value, char *addr, int bytes)
    {
    xdata int i;

for (i = 0; i < bytes; i++)
        value[i] = addr[i];
    }

/*
    Routines for driving the lcd display
*/ void lcd_init(void)
    {
    unsigned long timeout;
    INT1 = 0;
    INT0 = 0;
    RT2 = one;
    LCD = 0x38;
    RT2 = 0;
    timeout = time + 1L;
    while(time <= timeout);
    RT2 = one;
    LCD = 0x38;
    RT2 = 0;
    timeout = time + 1L;
    while(time <= timeout);
    RT2 = one;
    LCD = 0x38;
    RT2 = 0;
    write_lcd(0x0c, 0);
    write_lcd(0x38, 0);
    write_lcd(0x01, 0);
    write_lcd(0x06, 0);
```

```
                } void write_lcd(char info, bit rs)
                {
                while(lcd_busy());
                INT1 = rs;
                INT0 = 0;
                RT2 = one;
                LCD = info;
                RT2 = 0;
                } char read_lcd(void)
                {
                idata char readc;
                INT1 = 0;
                INT0 = one;
                RT2 = one;
                readc = LCD;
                RT2 = 0;
                return (readc);
                } void clearline(void)
                {
                unsigned char w;

for(w = 0; w < 20; w++)
                        write_lcd(0x20, 1);
                } void lastline(void)
                {
                row4();
                clearline();
                row4();
                write_lcd(0xe2, 0);
                } bit lcd_busy(void)
                {
                bit fl;
                char tch;

fl = one;
                INT1 = 0;
                INT0 = one;
                RT2 = one;
                tch = LCD;
                RT2 = 0;
                if (!(tch & 0x80))
                        fl = 0;
                return(fl);
                }
```

```
/*
        keypad routines
*/ include <stdio.h>
include "reg552.h"
#define one (bit) 1;

void decode_key(void);
extern void serial_data(void);
extern char read_lcd(void);
extern void write_lcd(char, bit);

extern idata bit mains, manualht, manualmo, manmoop;
extern xdata unsigned char pwmm0, orpmcount, pulse2;
extern idata long i1;

idata bit kflag, keypress, rbit;
xdata char newkey, keybuffer[15];
xdata unsigned char kcountu, kcountd;

void read_keypad(char *input)
    {
    /*          */
    xdata char nkey, row0, row1, row2, row3, flag;

nkey = 0x00;
    row0 = 0;
    row1 = 0;
    row2 = 0;
    row3 = 0;
    flag = 0;
    CT3I = 0;
    row3 = P5;
    row3 >>= 3;
    CT3I = one;
    CT2I = 0;
    row2 = P5;
    row2 >>= 3;
    CT2I = one;
    CT1I = 0;
    row1 = P5;
    row1 >>= 3;
    CT1I = one;
    CT0I = 0;
    row0 = P5;
    row0 >>= 3;
    CT0I = one;

row0 = ~row0 & 0x1f;
    row1 = ~row1 & 0x1f;
    row2 = ~row2 & 0x1f;
    row3 = ~row3 & 0x1f;
    if (row3)
        flag++;
    if (row2)
        flag++;
    if (row1)
        flag++;
    if (row0)
        flag++;
    if (flag == 1) {
        if (kcountu > 2) {
            if (row0) {
                switch (row0) {
                    case 0x01:
                        /* A */
                        nkey = 0x41;
                        break;
                    case 0x02:
```

```
                    /* 9 */
                    nkey = 0x39;
                    break;
            case 0x04:
                    /* 8 */
                    nkey = 0x38;
                    break;
            case 0x08:
                    /* 7 */
                    nkey = 0x37;
                    break;
            case 0x10:
                    /* E */
                    nkey = 0x45;
                    break;
            default:
                    /* multiple key or no key
                       null  (may need to be cancel or escape for
                       scanf routine */
                    nkey = 0x00;
                    break;
            }
    }
    else if (row1) {
            switch (row1) {
            case 0x01:
                    /* B */
                    nkey = 0x42;
                    break;
            case 0x02:
                    /* 6 */
                    nkey = 0x36;
                    break;
            case 0x04:
                    /* 5 */
                    nkey = 0x35;
                    break;
            case 0x08:
                    /* 4 */
                    nkey = 0x34;
                    break;
            case 0x10:
                    /* F */
                    nkey = 0x46;
                    break;
            default:
                    /* multiple key or no key
                       null  (may need to be cancel or escape for
                       scanf routine */
                    nkey = 0x00;
                    break;
            }
    }
    else if (row2) {
            switch (row2) {
            case 0x01:
                    /* C */
                    nkey = 0x43;
                    break;
            case 0x02:
                    /* 3 */
                    nkey = 0x33;
                    break;
            case 0x04:
                    /* 2 */
                    nkey = 0x32;
                    break;
            case 0x08:
                    /* 1 */
                    nkey = 0x31;
                    break;
            case 0x10:
                    /* G */
                    nkey = 0x47;
                    break;
```

```c
                            default:
                                /* multiple key or no key
                                    null  (may need to be cancel or escape for
                                    scanf routine */
                                nkey = 0x00;
                                break;
                        }
                    }
                    else {
                        switch (row3) {
                            case 0x01:
                                /* backspace (was D) */
                                nkey = 0x08;
                                break;
                            case 0x02:
                                /* <cr> */
                                nkey = 0x0d;
                                break;
                            case 0x04:
                                /* . */
                                nkey = 0x2e;
                                break;
                            case 0x08:
                                /* 0 */
                                nkey = 0x30;
                                break;
                            case 0x10:
                                /* - */
                                nkey = 0x2d;
                                break;
                            default:
                                /* multiple key or no key
                                    null  (may need to be cancel or escape for
                                    scanf routine */
                                nkey = 0x00;
                                break;
                        }
                    }
                    if (kflag) {
                        keypress = one;
                        kcountd = 0;
                        kflag = 0;
                        rbit = 0;
                    }
                    else {
                        rbit = one;
                    }
                    *input = nkey;
                }
                else {
                    kcountu++;
                    kcountd = 0;
                }
            }
            else if (flag > 1) {
                kcountu = 0;
                kcountd = 0;
                rbit = 0;
                kflag = 0;
            }
            else {
                if (kcountd > 2) {
                    kflag = one;
                    kcountu = 0;
                    rbit = 0;
                }
                else {
                    kcountd++;
                    kcountu = 0;
                    rbit = 0;
                }
            }
        }
```

```c
void decode_key(void)
{
    if (keypress) {
        switch (newkey) {
            case 'E':
                if (mains) {
                    if (manualmo) {
                        if (manmoop) {
                            manmoop = 0;
                            P4 |= 0x04;
                        }
                        else {
                            P4 &= 0xfb;
                            i1 = 0;
                            orpmcount = 0;
                            manualmo = 0;
                        }
                    }
                    else {
                        P4 |= 0x04;
                        manualmo = one;
                    }
                    keypress = 0;
                }
                break;
            case 'G':
                if (!manualht) {
                    manualht = one;
                    pulse2 = 0;
                    keypress = 0;
                    manualmo = one;
                    P4 |= 0x04;
                    keypress = 0;
                }
                break;
            default:
                break;
        }
    }
} void getinput(void)
{
    unsigned char place, loc;
    char tch;

place = 0;
    do {
        tch = _getkey();
        if (tch == 0x08) {
            if (place > 0) {
                ungetchar(0x00);
                loc = (read_lcd()) & 0x7f;
                switch(loc) {
                    case 0x00:
                        loc = 0xe7;
                        break;
                    case 0x40:
                        loc = 0xa7;
                        break;
                    case 0x14:
                        loc = 0x93;
                        break;
                    case 0x54:
                        loc = 0xd3;
                        break;
                    default:
                        loc--;
                        break;
                }
                loc |= 0x80;
                write_lcd(loc, 0);
                write_lcd (0x20, 1);
                write_lcd(loc, 0);
```

```
                    place--;
                }
            }
            else if (tch == 0x0d)
                keybuffer[place] = '\0';
            else {
                keybuffer[place] = tch;
                write_lcd(tch, 1);
                place++;
                if (place > 14) {
                    place = 14;
                    keybuffer[14] = '\0';
                }
            }
        } while (tch != 0x0d);
    } char _getkey ()
    {
    while (!keypress)
        serial_data();
    keypress = 0;
    return (newkey);
    }
```

```
/*
    definitions for lcd display.
*/
#define row1()  (write_lcd(0x80, 0))

#define row2()  (write_lcd(0xc0, 0))
#define row3()  (write_lcd(0x94, 0))
#define row4()  (write_lcd(0xd4, 0))
```

```c
/*
    eeprom backup definitions
*/ struct lut_entry
    {
    char label[16];
    unsigned char gelw[2];
    float mhrt[2][3];
    float scon[3];
    };

define tempsave (unsigned int *) 0x20a00L define mslp_back (char *) 0x24000L /* float */
define pb1_back (char *) 0x24004L /* int */
#define ib1_back (char *) 0x24006L /* int */
#define pb2_back (char *) 0x24008L /* int */
#define ib2_back (char *) 0x2400aL /* int */
#define ppr_back (char *) 0x2400cL /* int */
#define rate_back (char *) 0x2400eL  /* float */
#define rpm_back (char *) 0x24012L /* int */
#define a0_back (char *) 0x24014L /* char */
#define a1_back (char *) 0x24015L /* char */
#define hrate_back (char *) 0x24016L /* float */
#define torquec_back (char *) 0x2401aL /* float */
#define eff_back (char *) 0x2401eL /* float */
#define pb3_back (char *) 0x24022L /* int */
#define ib3_back (char *) 0x24024L /* int */
#define nlc_back (char *) 0x24026L /* float */
#define storq_back (char *) 0x2402aL /* int */
#define otorq_back (char *) 0x2402cL /* int */
#define tsl_back (char *) 0x2402eL /* float */
#define toff_back (char *) 0x24032L /* float */
#define zt_back (char *) 0x24036L /* float */
#define za_back (char *) 0x2403aL /* float */
#define mtemp_back (char *) 0x2403eL /* float */
#define sc_back (char *) 0x24042L  /* char */
#define ffwdm_back (char *) 0x24043L /* float */
#define bht_back (char *) 0x24047L /* float */
#define vtp_back (char *) 0x2404bL /* float */
#define bpm_back (char *) 0x2404fL /* float */
#define stt_back (char *) 0x24053L /* float */
#define lut_ptr ((struct lut_entry *) 0x24057L) /* 5 x 16 chars + 2 chars + 9 floats */
/* next is 0x241a1 */ define TORQUEC 1.93    /* oz in / amp */
define GEAR 30.959
#define EFF 0.66    /* percent */
#define PPR 500  /* pulses per revolution of the optical encoder */
#define RPM_CONST 0.003876  /* 60 sec/min / (GEAR * PPR) */
#define TORQUE_GEAR 39.4356 /* TORQUEC * EFF * GEAR */
#define TORQUE_COUNTS 0.000977517  /* 1 AMP / 1023 COUNTS */
```

```c
/*
Module:   reg552.h
Creation: 01/28/94

Purpose: Register declarations for the Philips 8xC592 processor.

References:
    Philips Semiconductors, Data Handbook, "80C51-Based 8-Bit Micro-
        controllers", March 1993
*/
/******************************************************************************/
/*********************  Byte Register Declarations  ********************/
#define uchar unsigned char
sfr P0      = 0X80;     /* Port 0                             */
sfr SP      = 0X81;     /* Stack pointer                      */
sfr DPL     = 0X82;     /* Data pointer low                   */
sfr DPH     = 0X83;     /* Data pointer high                  */
sfr PCON    = 0X87;     /* Power control                      */
sfr TCON    = 0X88;     /* Timer control                      */
sfr TMOD    = 0X89;     /* Timer mode                         */
sfr TL0     = 0X8A;     /* Timer low 0                        */
sfr TL1     = 0X8B;     /* Timer low 1                        */
sfr TH0     = 0X8C;     /* Timer high 0                       */
sfr TH1     = 0X8D;     /* Timer high 1                       */
sfr P1      = 0X90;     /* Port 1                             */
sfr S0CON   = 0X98;     /* Serial 0 control                   */
sfr S0BUF   = 0X99;     /* Serial 0 data buffer               */
sfr P2      = 0XA0;     /* Port 2                             */
sfr IEN0    = 0XA8;     /* Interrupt enable 0                 */
sfr CML0    = 0XA9;     /* Compare Low 0                      */
sfr CML1    = 0XAA;     /* Compare Low 1                      */
sfr CML2    = 0XAB;     /* Compare Low 2                      */
sfr CTL0    = 0XAC;     /* Capture Low 0                      */
sfr CTL1    = 0XAD;     /* Capture Low 1                      */
sfr CTL2    = 0XAE;     /* Capture Low 2                      */
sfr CTL3    = 0XAF;     /* Capture Low 3                      */
sfr P3      = 0XB0;     /* Port 3                             */
sfr IP0     = 0XB8;     /* Interrupt priority 0               */
sfr P4      = 0XC0;     /* Port 4                             */
sfr P5      = 0XC4;     /* Port 5                             */
sfr ADCON   = 0XC5;     /* Adc control                        */
sfr ADCH    = 0XC6;     /* A/D converter high                 */
sfr TM2IR   = 0XC8;     /* Timer 2 interrupt flag register    */
sfr CMH0    = 0XC9;     /* Compare high 0                     */
sfr CMH1    = 0XCA;     /* Compare high 1                     */
sfr CMH2    = 0XCB;     /* Compare high 2                     */
sfr CTH0    = 0XCC;     /* Capture high 0                     */
sfr CTH1    = 0XCD;     /* Capture high 1                     */
sfr CTH2    = 0XCE;     /* Capture high 2                     */
sfr CTH3    = 0XCF;     /* Capture high 3                     */
sfr PSW     = 0XD0;     /* Program status word                */
sfr ACC     = 0XE0;     /* Accumulator                        */
sfr IEN1    = 0XE8;     /* Interrupt enable 1                 */
sfr TM2CON  = 0XEA;     /* Timer 2 control                    */
sfr CTCON   = 0XEB;     /* Capture control                    */
sfr TML2    = 0XEC;     /* Timer low 2                        */
sfr TMH2    = 0XED;     /* Timer high 2                       */
sfr STE     = 0XEE;     /* Set enable                         */
sfr RTE     = 0XEF;     /* Reset/toggle enable                */
sfr B       = 0XF0;     /* B register                         */
sfr IP1     = 0XF8;     /* Interrupt priority 1               */
sfr PWM0    = 0XFC;     /* PWM register 0                     */
sfr PWM1    = 0XFD;     /* PWM register 1                     */
sfr PWMP    = 0XFE;     /* PWM prescaler                      */
sfr T3      = 0XFF;     /* Timer 3                            */
sfr S1ADR   = 0XDB;     /*                                    */
sfr S1DAT   = 0XDA;     /*                                    */
sfr S1STA   = 0XD9;     /*                                    */
sfr S1CON   = 0XD8;     /*                                    */
/******************************************************************************/
/********************  Bit Register Declarations  ********************/
/************
 P0 - Port 0
************/
```

```
sbit AD0    = 0X80;    /* P0 bit 0 - Address/Data line 0           */
sbit AD1    = 0X81;    /* P0 bit 1 - Address/Data line 1           */
sbit AD2    = 0X82;    /* P0 bit 2 - Address/Data line 2           */
sbit AD3    = 0X83;    /* P0 bit 3 - Address/Data line 3           */
sbit AD4    = 0X84;    /* P0 bit 4 - Address/Data line 4           */
sbit AD5    = 0X85;    /* P0 bit 5 - Address/Data line 5           */
sbit AD6    = 0X86;    /* P0 bit 6 - Address/Data line 6           */
sbit AD7    = 0X87;    /* P0 bit 7 - Address/Data line 7           */

/*********************
    TCON - Timer control
*********************/
sbit IT0    = 0X88;    /* TCON bit 0 - Interrupt 0 type control bit  */
sbit IE0    = 0X89;    /* TCON bit 1 - Interrupt 0 edge flag         */
sbit IT1    = 0X8A;    /* TCON bit 2 - Interrupt 1 type control bit  */
sbit IE1    = 0X8B;    /* TCON bit 3 - Interrupt 1 edge flag         */
sbit TR0    = 0X8C;    /* TCON bit 4 - Timer 0 run control bit       */
sbit TF0    = 0X8D;    /* TCON bit 5 - Timer 0 overflow flag         */
sbit TR1    = 0X8E;    /* TCON bit 6 - Timer 1 run control bit       */
sbit TF1    = 0X8F;    /* TCON bit 7 - Timer 1 overflow flag         */

/************
    P1 - Port 1
************/
sbit CT0I   = 0X90;    /* P1 bit 0 - __                              */
sbit CT1I   = 0X91;    /* P1 bit 1 -   \__  Capture timer input      */
sbit CT2I   = 0X92;    /* P1 bit 2 -   __/  signals for timer T2     */
sbit CT3I   = 0X93;    /* P1 bit 3 -                                 */
sbit T2     = 0X94;    /* P1 bit 4 - T2 event input                  */
sbit RT2    = 0X95;    /* P1 bit 5 - T2 timer reset signal           */
sbit SCL    = 0X96;    /* P1 bit 6 -           */
sbit SDA    = 0X97;    /* P1 bit 7 -           */

/************************
    S0CON - Serial 0 control
************************/
sbit RI     = 0X98;    /* S0CON bit 0 - Receive interrupt flag       */
sbit TI     = 0X99;    /* S0CON bit 1 - Transmit interrupt flag      */
sbit RB8    = 0X9A;    /* S0CON bit 2 - See manual                   */
sbit TB8    = 0X9B;    /* S0CON bit 3 - See manual                   */
sbit REN    = 0X9C;    /* S0CON bit 4 - Enable serial reception      */
sbit SM2    = 0X9D;    /* S0CON bit 5 - Multiprocessor enable        */
sbit SM1    = 0X9E;    /* S0CON bit 6 - Serial port mode             */
sbit SM0    = 0X9F;    /* S0CON bit 7 - Serial port mode             */

/************
    P2 - Port 2
************/
sbit A8     = 0XA0;    /* P2 bit 0 - Address line 8                  */
sbit A9     = 0XA1;    /* P2 bit 1 - Address line 9                  */
sbit A10    = 0XA2;    /* P2 bit 2 - Address line 10                 */
sbit A11    = 0XA3;    /* P2 bit 3 - Address line 11                 */
sbit A12    = 0XA4;    /* P2 bit 4 - Address line 12                 */
sbit A13    = 0XA5;    /* P2 bit 5 - Address line 13                 */
sbit A14    = 0XA6;    /* P2 bit 6 - Address line 14                 */
sbit A15    = 0XA7;    /* P2 bit 7 - Address line 15                 */

/************************
    IEN0 - Interrupt enable 0
************************/
sbit EX0    = 0XA8;    /* IEN0 bit 0 - Enable external interrupt 0         */
sbit ET0    = 0XA9;    /* IEN0 bit 1 - Enable timer 0 overflow interrupt   */
sbit EX1    = 0XAA;    /* IEN0 bit 2 - Enable external interrupt 1         */
sbit ET1    = 0XAB;    /* IEN0 bit 3 - Enable timer 1 overflow interrupt   */
sbit ES0    = 0XAC;    /* IEN0 bit 4 - Enable serial port 0 interrupt      */
sbit ES1    = 0XAD;    /* IEN0 bit 5 - Enable CAN interrupt                */
sbit EAD    = 0XAE;    /* IEN0 bit 6 - Enable ADC interrupt                */
sbit EA     = 0XAF;    /* IEN0 bit 7 - Enable global interrupt             */

/************
    P3 - Port 3
************/
sbit RXD    = 0XB0;    /* P3 bit 0 - Serial port 0 input             */
sbit TXD    = 0XB1;    /* P3 bit 1 - Serial port 0 output            */
sbit INT0   = 0XB2;    /* P3 bit 2 - External interrupt 0            */
```

```
sbit INT1   = 0XB3;     /* P3 bit 3 - External interrupt 1                      */
sbit T0     = 0XB4;     /* P3 bit 4 - Timer 0 external input                    */
sbit T1     = 0XB5;     /* P3 bit 5 - Timer 1 external input                    */
sbit WR     = 0XB6;     /* P3 bit 6 - External data memory write strobe         */
sbit RD     = 0XB7;     /* P3 bit 7 - External data memory read strobe          */

/****************************
   IP0 - Interrupt priority 0
****************************/
sbit PX0    = 0XB8;     /* IP0 bit 0 - External interrupt 0 priority level */
sbit PT0    = 0XB9;     /* IP0 bit 1 - Timer 0 interrupt priority level    */
sbit PX1    = 0XBA;     /* IP0 bit 2 - External interrupt 1 priority level */
sbit PT1    = 0XBB;     /* IP0 bit 3 - Timer 1 interrupt priority level    */
sbit PS0    = 0XBC;     /* IP0 bit 4 - SIO0 interrupt priority level       */
sbit PS1    = 0XBD;     /* IP0 bit 5 - CAN interrupt priority level        */
sbit PAD    = 0XBE;     /* IP0 bit 6 - ADC priority interrupt level        */

/****************************
   PSW - Program status word
****************************/
sbit P      = 0XD0;     /* PSW bit 0 - Parity flag                */
sbit F1     = 0XD1;     /* PSW bit 1 - User definable flag        */
sbit OV     = 0XD2;     /* PSW bit 2 - Overflow flag              */
sbit RS0    = 0XD3;     /* PSW bit 3 - Register bank select 0     */
sbit RS1    = 0XD4;     /* PSW bit 4 - Register bank select 1     */
sbit F0     = 0XD5;     /* PSW bit 5 - Flag 0                     */
sbit AC     = 0XD6;     /* PSW bit 6 - Auxiliary carry flag       */
sbit CY     = 0XD7;     /* PSW bit 7 - Carry flag                 */

/******************************
      S1CON
******************************/
sbit CR0    = 0XD8;     /*         */
sbit CR1    = 0XD9;     /*         */
sbit AA     = 0XDA;     /*         */
sbit SI     = 0XDB;     /*         */
sbit STO    = 0XDC;     /*         */
sbit STA    = 0XDD;     /*         */
sbit ENS1   = 0XDE;     /*         */
sbit CR2    = 0XDF;     /*         */

/******************
   ACC - Accumulator
******************/
sbit ACC_0  = 0XE0;     /* ACC bit 0      */
sbit ACC_1  = 0XE1;     /* ACC bit 1      */
sbit ACC_2  = 0XE2;     /* ACC bit 2      */
sbit ACC_3  = 0XE3;     /* ACC bit 3      */
sbit ACC_4  = 0XE4;     /* ACC bit 4      */
sbit ACC_5  = 0XE5;     /* ACC bit 5      */
sbit ACC_6  = 0XE6;     /* ACC bit 6      */
sbit ACC_7  = 0XE7;     /* ACC bit 7      */

/**************************
   IEN1 - Interrupt enable 1
**************************/
sbit ECT0   = 0XE8;     /* IEN1 bit 0 - Enable T2 capture reg. 0 interrupt */
sbit ECT1   = 0XE9;     /* IEN1 bit 1 - Enable T2 capture reg. 1 interrupt */
sbit ECT2   = 0XEA;     /* IEN1 bit 2 - Enable T2 capture reg. 2 interrupt */
sbit ECT3   = 0XEB;     /* IEN1 bit 3 - Enable T2 capture reg. 3 interrupt */
sbit ECM0   = 0XEC;     /* IEN1 bit 4 - Enable T2 comparator 0 interrupt   */
sbit ECM1   = 0XED;     /* IEN1 bit 5 - Enable T2 comparator 1 interrupt   */
sbit ECM2   = 0XEE;     /* IEN1 bit 6 - Enable T2 comparator 2 interrupt   */
sbit ET2    = 0XEF;     /* IEN1 bit 7 - Enable T2 overflow interrupt(s)    */

/**************
   B - B register
**************/
sbit B_0    = 0XF0;     /* B bit 0        */
sbit B_1    = 0XF1;     /* B bit 1        */
sbit B_2    = 0XF2;     /* B bit 2        */
sbit B_3    = 0XF3;     /* B bit 3        */
sbit B_4    = 0XF4;     /* B bit 4        */
sbit B_5    = 0XF5;     /* B bit 5        */
sbit B_6    = 0XF6;     /* B bit 6        */
```

```
sbit B_7     = 0XF7;     /* B bit 7                                          */

/***************************
  IP1 - Interrupt priority 1
***************************/
sbit PCT0    = 0XF8;     /* IP1 bit 0 - T2 cap.  reg. 0 int. priority level  */
sbit PCT1    = 0XF9;     /* IP1 bit 1 - T2 cap.  reg. 1 int. priority level  */
sbit PCT2    = 0XFA;     /* IP1 bit 2 - T2 cap.  reg. 2 int. priority level  */
sbit PCT3    = 0XFB;     /* IP1 bit 3 - T2 cap.  reg. 3 int. priority level  */
sbit PCM0    = 0XFC;     /* IP1 bit 4 - T2 comp. reg. 0 int. priority level  */
sbit PCM1    = 0XFD;     /* IP1 bit 5 - T2 comp. reg. 1 int. priority level  */
sbit PCM2    = 0XFE;     /* IP1 bit 6 - T2 comp. reg. 2 int. priority level  */
sbit PT2     = 0XFF;     /* IP1 bit 7 - T2 overflow int.(s) priority level   */
```

What is claimed is:

1. A method of testing for the occurrence of chemical crosslinking of a fluid, comprising steps of:

(a) placing in a vessel a fluid having a crosslinking agent;

(b) rotating a paddle through the fluid in the vessel at substantially a constant rotational speed;

(c) sensing a paddle torque parameter at sequential times and encoding digital signals to define digital torque data representing values of the sensed torque parameter and to define digital time data representing corresponding sequential times;

(d) determining, in response to digital torque data and digital time data, a baseline torque parameter value and a change in the digital torque data representing increasing torque of the paddle; and (e) determining, in response to the baseline torque parameter value and the change in the digital torque data, a crosslink time for the fluid.

2. A method as defined in claim 1, further comprising:

heating the fluid;

sensing temperature of the fluid during the sequential times and encoding digital signals to define digital temperature data at corresponding sequential times; and determining, in response to the crosslink time and the digital temperature data, a crosslink temperature.

3. A method as defined in claim 1, wherein step (c) includes converting nondigital torque parameter signals into the encoded digital torque data.

4. A method as defined in claim 1, wherein step (e) includes computing the crosslink time as the time point at which a line containing the change in the digital torque data coincides with the baseline torque parameter value.

5. A method as defined in claim 1, wherein step (b) includes energizing a motor connected to the paddle so that the motor rotates the paddle to maintain a constant rotational speed, and wherein step (c) includes sensing the level of energization of the motor at sequential times as the paddle torque parameter and encoding digital signals to define digital energization data representing sensed energization levels as the digital torque data.

6. A method as defined in claim 5, wherein step (e) includes computing the crosslink time as the time point at which a line containing a maximum change in the digital energization data coincides with the baseline torque parameter value.

7. A method as defined in claim 6, further comprising:

heating the fluid;

sensing temperature of the fluid during the sequential times and encoding digital signals to define digital temperature data at corresponding sequential times; and determining, in response to the crosslink time and the digital temperature data, a crosslink temperature.

8. A method of testing for the occurrence of chemical crosslinking of a fluid, comprising steps of:

(a) placing in a vessel a fluid having a crosslinking agent;.

(b) rotating a paddle through the fluid in the vessel, including energizing, with a programmed electronic controller, a motor connected to the paddle so that the motor rotates the paddle, wherein the electronic controller is programmed for sensing rotational speed of the paddle and changing the level of energization of the motor as needed to maintain a constant rotational speed;

(c) sensing energization of the motor at sequential times and storing in a digital memory of the electronic controller encoded digital signals defining digital energization data representing sensed energization levels;

(d) determining, in the electronic controller in response to stored digital energization data and digital time data, a baseline energization level and a maximum rate of change of the energization data;

(e) determining, in the electronic controller in response to the baseline energization level and the maximum rate of change of the energization data, a crosslink time for the fluid; and (f) displaying the crosslink time.

9. A method as defined in claim 8, further comprising:

heating the fluid;

sensing, with the electronic controller, temperature of the fluid during the sequential times and storing in the digital memory of the electronic controller encoded signals defining sensed temperatures at corresponding sequential times;

determining, in the electronic controller in response to the crosslink time and the stored encoded signals defining sensed temperatures, a crosslink temperature; and displaying the crosslink temperature.

10. A method as defined in claim 8, wherein step (c) includes converting nondigital energization signals into the encoded digital signals.

11. A method as defined in claim 8, wherein step (e) includes computing the crosslink time as the time point at which a line containing the maximum rate of change of the energization data coincides with the baseline energization level.

12. A method of testing for the occurrence of chemical crosslinking of a fluid, comprising steps of:

(a) placing in a vessel a fluid having a crosslinking agent;

(b) heating the fluid;

(c) rotating a paddle through the fluid in the vessel, including energizing, with a programmed electronic controller, a motor connected to the paddle so that the motor rotates the paddle, wherein the electronic controller is programmed for periodically sensing rotational speed of the paddle and changing the level of energization of the motor as needed to maintain a constant rotational speed;

(d) sensing a paddle torque parameter at sequential times and storing in a digital memory of the electronic controller encoded digital signals defining digital torque data representing sensed paddle torque parameter levels;

(e) sensing temperature of the fluid during the sequential times and storing in the digital memory of the electronic controller encoded digital signals defining digital temperature data representing sensed temperatures at corresponding sequential times;

(f) determining, in the electronic controller in response to the digital temperature data, when a temperature rise first occurs;

(g) determining, in the electronic controller in response to the digital torque data and digital time data, when a minimum rate of change of the digital torque data occurs;

(h) determining, in the electronic controller in response to stored digital torque data, a baseline paddle torque parameter value, including computing an average of the digital torque data over a time period after step (f);

(i) determining a maximum rate of change of the digital torque data;

(j) determining, in the electronic controller in response to the baseline paddle torque parameter value and the maximum rate of change of the digital torque data, a crosslink time for the fluid, including computing the crosslink time from the specific digital torque data and the time data defining the maximum rate of change and from the baseline paddle torque parameter value;

(k) determining, in the electronic controller in response to the crosslink time and the stored encoded signals defining sensed temperatures, a crosslink temperature at the crosslink time; and (l) displaying the crosslink time and temperature.

13. A method as defined in claim 12, wherein sensing a paddle torque parameter includes sensing the level of energization of the motor.

14. A method as defined in claim 12, wherein the paddle is a double helix paddle.

15. A method as defined in claim 12, wherein step (i) includes:

(i1) computing a slope using linear regression with torque data in the digital memory and corresponding time data;

(i2) setting the computed slope as an interim maximum slope;

(i3) computing a subsequent slope in response to subsequent torque data and corresponding time data and comparing this subsequent slope with the interim maximum slope, wherein if the subsequent slope is not greater than the interim maximum slope, repeat step (i3) up to a predetermined number of times, and if the subsequent slope is greater than the interim maximum slope, reset the interim maximum slope equal to the subsequent slope and repeat step (i3); and (i4) counting the number of times step (i3) is performed without the interim maximum slope being reset and setting the interim maximum slope as the maximum rate of change of the digital torque data in response to the count equalling a predetermined number.

16. A method as defined in claim 15, wherein sensing torque includes sensing the level of energization of the motor.

17. A method as defined in claim 16, wherein the paddle is a double helix paddle.

* * * * *